US009062289B2

(12) United States Patent
Gold et al.

(10) Patent No.: US 9,062,289 B2
(45) Date of Patent: Jun. 23, 2015

(54) DIFFERENTIATION OF PRIMATE PLURIPOTENT STEM CELLS TO CARDIOMYOCYTE-LINEAGE CELLS

(75) Inventors: Joseph D. Gold, San Francisco, CA (US); Mohammad Hassanipour, Danville, CA (US)

(73) Assignee: Asterias Biotherapeutics, Inc., Menlo Park, CA (US)

( * ) Notice: Subject to any disclaimer, the term of this patent is extended or adjusted under 35 U.S.C. 154(b) by 602 days.

(21) Appl. No.: 11/471,916

(22) Filed: Jun. 20, 2006

(65) Prior Publication Data

US 2007/0010012 A1   Jan. 11, 2007

Related U.S. Application Data

(60) Provisional application No. 60/693,141, filed on Jun. 22, 2005.

(51) Int. Cl.
*C12N 5/00* (2006.01)
*C12N 5/077* (2010.01)

(52) U.S. Cl.
CPC ........ *C12N 5/0657* (2013.01); *C12N 2501/155* (2013.01); *C12N 2501/16* (2013.01); *C12N 2506/02* (2013.01); *C12N 2501/105* (2013.01)

(58) Field of Classification Search
CPC ... A61K 2300/00; A61K 38/19; A61K 38/30; C12N 5/0657; C12N 5/0662; C12N 5/0692
See application file for complete search history.

(56) References Cited

U.S. PATENT DOCUMENTS

| | | | |
|---|---|---|---|
| 5,543,318 A | 8/1996 | Smith et al. | |
| 5,733,727 A | 3/1998 | Field | |
| 5,843,780 A | 12/1998 | Thomson | |
| 5,928,943 A | 7/1999 | Franz et al. | |
| 5,942,435 A | 8/1999 | Wheeler | |
| 6,015,671 A | 1/2000 | Field | |
| 6,099,832 A | 8/2000 | Mickle et al. | |
| 6,110,459 A | 8/2000 | Mickle et al. | |
| 6,245,566 B1 | 6/2001 | Gearhart et al. | |
| 6,261,836 B1 | 7/2001 | Cech et al. | |
| 6,387,369 B1 | 5/2002 | Pittenger et al. | |
| 6,399,300 B1 | 6/2002 | Field | |
| 6,534,052 B1 | 3/2003 | Xiao et al. | |
| 6,610,826 B1 | 8/2003 | Meyer et al. | |
| 7,425,448 B2 | 9/2008 | Xu | |
| 7,452,718 B2 * | 11/2008 | Gold et al. | 435/377 |
| 8,168,433 B2 | 5/2012 | Gehman et al. | |
| 8,298,606 B2 | 10/2012 | Healy et al. | |
| 2002/0061837 A1 | 5/2002 | Lough et al. | |
| 2002/0142457 A1 | 10/2002 | Umezawa et al. | |
| 2002/0146678 A1 * | 10/2002 | Benvenisty | 435/4 |
| 2002/0151053 A1 | 10/2002 | Carpenter et al. | |
| 2004/0005701 A1 * | 1/2004 | Xu et al. | 435/363 |
| 2004/0022367 A1 * | 2/2004 | Talalai | 379/10.01 |
| 2004/0096505 A1 | 5/2004 | Woerly | |
| 2005/0037489 A1 | 2/2005 | Gepstein et al. | |
| 2005/0054092 A1 | 3/2005 | Xu et al. | |
| 2005/0164382 A1 * | 7/2005 | Xu | 435/366 |
| 2005/0214938 A1 | 9/2005 | Xu et al. | |
| 2005/0227353 A1 | 10/2005 | Mummery | |
| 2005/0266554 A1 * | 12/2005 | D'Amour et al. | 435/366 |
| 2008/0213389 A1 | 9/2008 | Lelkes et al. | |
| 2009/0017465 A1 | 1/2009 | Xu | |
| 2009/0047739 A1 | 2/2009 | Xu et al. | |
| 2010/0099160 A1 | 4/2010 | Jiang et al. | |
| 2010/0304482 A1 | 12/2010 | Deshayes et al. | |

FOREIGN PATENT DOCUMENTS

| | | |
|---|---|---|
| AU | 729377 B2 | 2/2001 |
| WO | WO 92/13066 A1 | 8/1992 |
| WO | WO 95/14079 A1 | 5/1995 |
| WO | WO-98/06420 | 2/1998 |
| WO | WO 99/49015 A2 | 9/1999 |
| WO | WO-99/53021 | 10/1999 |
| WO | WO 00/06701 A1 | 2/2000 |
| WO | WO 00/70021 A2 | 11/2000 |
| WO | WO 00/78119 A2 | 12/2000 |
| WO | WO 01/22978 A2 | 4/2001 |
| WO | WO 01/48151 A1 | 7/2001 |
| WO | WO 01/51616 A2 | 7/2001 |
| WO | WO 01/53465 A1 | 7/2001 |
| WO | WO 01/68814 A2 | 9/2001 |
| WO | WO 02/09650 A2 | 2/2002 |
| WO | WO 02/10347 | 2/2002 |
| WO | WO 02/13760 A2 | 2/2002 |
| WO | WO 02/19893 A2 | 3/2002 |
| WO | WO 02/30206 A1 | 4/2002 |
| WO | WO 02/083864 A2 | 10/2002 |
| WO | WO 03/006950 A2 | 1/2003 |
| WO | WO 03/087296 | 10/2003 |
| WO | WO 2004/081205 A1 | 9/2004 |

OTHER PUBLICATIONS

De Pater E et al. 2009. Distinct phases of cardiomyocyte differentiation regulate growth of the zebrafish heart. Development 136: 1633-1641.*

(Continued)

*Primary Examiner* — Thaian N Ton
*Assistant Examiner* — Titilayo Moloye
(74) *Attorney, Agent, or Firm* — Krista P. Kauppinen; E. Stewart Mittler

(57) ABSTRACT

The present application describes the new methods for the differentiation of primate pluripotent stem cells into cardiomyocyte-lineage cells. The methods utilize sequential culturing of the primate pluripotent stem cells in certain growth factors to produce cardiomyocyte-lineage cells. In certain embodiments of the invention, the population of cells produced by the sequential culturing is further enriched for cardiomyocyte-lineage cells so as to produce a higher percentage of those cells.

23 Claims, 4 Drawing Sheets

(56) References Cited

OTHER PUBLICATIONS

Boheler K et al. 2002. Differentiation of pluripotent embryonic stem cells into cardiomyocytes. Circ Res 91: 189-201.*

Schuldiner et al. "Effects of eight growth factors on the differentiation of cells derived from human embryonic stem cells." Proc Natl Acad Sci U S A. ( 2000); 97(21): 11307-11312.*

Zhang et al. "Short-term BMP-4 treatment initiates mesoderm induction in human embryonic stem cells." Blood (Feb. 2008);111(4): pp. 1933-1941.*

Xu et al. "Feeder-free growth of undifferentiated human embryonic stem cells." Nat Biotechnol. (2001);19(10):971-974.*

Xu et al. "Basic Fibroblast Growth Factor Supports Undifferentiated Human Embryonic Stem Cell Growth Without Conditioned Medium." Stem cells (Mar. 2005); 23(3):pp. 315-323.*

Charron, F. & Nemer, M., "GATA transcription factors and cardiac development," *Semin. Cell Dev. Biol.* 10(1):85-91 (1999).

Alsan, B. & Schultheiss, T., "Regulation of avian cardiogenesis by Fgf8 signaling," *Development* 129:1935-43 (2002).

Andrée, B. et al., "BMP-2 induces ectopic expression of cardiac lineage markers and interferes with somite formation in chicken embryos," *Mech. Dev.* 70:119-31 (1998).

Antin, P. et al., "Regulation of avian precardiac mesoderm development by insulin and insulin-like growth factors," *J. Cell. Physiol.* 168:42-50 (1996).

Arai, A. et al., "Murine cardiac progenitor cells require visceral embryonic endoderm and primitive streak for terminal differentiation," Dev. Dynamics 210:344-53 (1997).

Barron, M. et al., "Requirement for BMP and FGF signaling during cardiogenic induction in non-precardiac mesoderm is specific, transient, and cooperative," *Dev. Dynamics* 218:383-93 (2000).

Bauwens, C. et al., "Development of a perfusion fed bioreactor for embryonic stem cell-derived cardiomyocyte generation: oxygen-mediated enhancement of cardiomyocyte output," *Biotechnol. Bioeng.* 90(4):452-61 (2005).

Behfar, A. et al., "Stem cell differentiation requires a paracrine pathway in the heart," *FASEB J.* 16:1558-66 (2002).

Caspi, O. & Gepstein, L., "Potential applications of human embryonic stem cell-derived cardiomyocytes," *Ann. N.Y. Acad. Sci.* 1015:285-298 (2004).

Claycomb, W. et al., "HL-1 cells: A cardiac muscle cell line that contracts and retains phenotypic characteristics of the adult cardiomyocyte," *Proc. Natl. Acad. Sci. USA* 95:2979-84 (1998).

Dang, S. et al., "Controlled, scalable embryonic stem cell differentiation culture," *Stem Cells* 22:275-82 (2004).

Doevendans, P. et al., "Differentiation of cardiomyocytes in floating embryoid bodies is comparable to fetal cardiomyocytes," *J. Mol. Cell Cardiol.* 32:839-51 (2000).

Fukuda, K., "Development of regenerative cardiomyocytes from mesenchymal stem cells for cardiovascular tissue engineering," *Artificial Organs* 25(3):187-93 (2001).

Gepstein, L., "Derivation and potential applications of human embryonic stem cells," *Circ. Res.* 91(10):866-76 (2002).

Goh, G. et al., "Molecular and phenotypic analyses of human embryonic stem cell-derived cardiomyocytes," *Thromb. Haemost.* 94:728-37 (2005).

Grépin, C. et al., "Enhanced cardiogenesis in embryonic stem cells overexpressing the GATA-4 transcription factor," *Development* 124:2387-95 (1997).

Gryshchenko, O. et al., "Outwards currents in embryonic stem cell-derived cardiomyocytes," *Pflügers Arch—Eur. J. Physiol.* 439:798-807 (2000).

Heng, B. et al., "Strategies for directing the differentiaion of stem cells into the cardiomyogenic lineage in vitro," *Cardiovascular Res.* 62:34-42 (2004).

Itskovitz-Eldor, J. et al., "Differentiation of human embronic stem cells into embryoid bodies comprising the three embryonic germ layers," *Molec. Med.* 6(2):88-95 (2000).

Johansson, B. & Wiles, M., "Evidence for involvement of activin A and bone morphogenetic protein 4 in mammalian mesoderm and hematopoietic development," *Molec. Cell. Biol.* 15(1):141-51 (1995).

Kawai, T. et al., "Efficient cardiomyogenic differentiation of embryonic stem cell by fibroblast growth factor 2 and bone morphogenetic protein 2," *Circ. J.* 68:691-702 (2004).

Kehat, I. et al., "Electromechanical integration of cardiomyocytes derived from human embryonic stem cells," *Nature Biotechnol.* 22(10):1282-89 (2004).

Kehat, I. et al., "Human embryonic stem cells can diffrentiate into myocytes with structural and functional properties of cardiomyocytes," *J. Clin. Invest.* 108(3):407-14 (2001).

Kehat, I. et al., "Long term high-resolution, electrophysiological assessment of human embryonic stem cell derived cardiomyocytes: A novel in vitro model for the human heart," *Circulation* 102(18 Suppl. II):II-4 Abstract 6 (2000).

Kessler, P. & Byrne, B., "Myoblast cell grafting into heart muscle: Cellular biology and potential applications," *Annu. Rev. Physiol.* 61:219-42 (1999).

Klug, M. et al., "Genetically selected cardiomyocytes from differentiating embryonic stem cells form stable intracardiac grafts," *J. Clin. Invest.* 98(1):216-24 (1996).

Kolossov, E. et al., "Functional characteristics of ES cell-derived cardiac precursor cells identified by tissue-specific expression of the green fluorescent protein," *J. Cell Biol.* 143(7):2045-56 (1998).

Ladd, A. et al., "Regulation of avian cardiac myogenesis by activin/TGFβ and bone morphogenetic proteins," *Dev. Biology* 204:407-19 (1998).

Laflamme, M. et al., "Formation of human myocardium in the rat heart from human embryonic stem cells," *Am. J. Pathol.* 167(3):663-71 (2005).

Lev, S. et al., "Differentiation pathways in human embryonic stem cell-derived cardiomyocytes," *Ann. N.Y. Acad. Sci.* 1047:50-65 (2005).

Li, R-K. et al., "Isolation of cardiomyocytes from human myocardium for primary cell culturing," *J. Tiss. Cult. Meth.* 15:147-54 (1993).

Liechty, K. et al., "Human mesenchymal stem cells engraft and demonstrate site-specific differentiation after in utero transplantation in sheep," *Nature Med.* 6:1282-86 (2000).

Lough, J. et al., "Combined BMP-2 and FGF-4, but neither factor alone, induces cardiogenesis in non-precardiac embryonic mesoderm," *Dev. Biology* 178:198-202 (1996).

Makino, S. et al., "Cardiomyocytes can be generated from marrow stromal cells in vitro," *J. Clin. Invest.* 103:697-705 (1999).

Maltsev, V. et al., "Embryonic stem cells differentiate in vitro into cardiomyocytes representing sinusnodal, atrial and ventricular cell types," *Mech. Dev.* 44:41-50 (1993).

Marvin, M. et al., "Inhibition of Wnt activity induces heart formation from posterior mesoderm," *Genes Dev.* 15:316-27 (2001).

Matsushita, T. et al., "Formation of cell junctions between grafted and host cardiomyocytes at the border zone of rat myocardial infarction," *Circulation* 100[suppl. II]:II-262-II-268 (1999).

McBurney, M. et al., "Control of muscle and neuronal differentiation in a cultured embryonal carcinoma cell line," *Nature* 299:165-67 (1982).

McDowell, N. & Gurdon, J., "Activin as a morphogen in *Xenopus* mesoderm induction," *Seminars in Cell & Devel. Biol.* 10:311-17 (1999).

Ménard, C. et al., "Transplantation of cardiac-committed mouse embryonic stem cells to infarcted sheep myocardium: preclinical study," The Lancet 366:1005-12 (2005).

Messina, E. et al., "Isolation and expansion of adult cardiac stem cells from human and murine heart," *Circ. Res.* 95:911-21 (2004).

Min, J.-Y. et al., "Transplantation of embryonic stem cells improves cardiac function in postinfacted rats," *J. Appl. Physiol.* 92:288-96 (2002).

Monzen, K. et al., "Bone morphogenetic proteins induce cardiomyocyte differentiation through the mitogen-activated protein kinase kinase kinase TAK1 and cardiac transcription factors Csx/Nkx-2.5 and GATA-4," *Mol. Cell Biol.* 19(10):7096-105 (1999).

(56) References Cited

OTHER PUBLICATIONS

Müller, M. et al., "Selection of ventricular-like cardiomyocytes from ES cells in vitro," *FASEB J.* 14:2540-48 (2000).
Mummery, C. et al., "Cardiomyocyte differentiation of mouse and human embryonic stem cells," *J. Anat.* 200:233-42 (2002).
Mummery, C. et al., "Differentiation of human embryonic stem cells to cardiomyocytes: Role of coculture with visceral endoderm-like cells," *Circulation* 107:2733-40 (2003).
Muslin, A. & Williams, L., "Well-defined growth factors promote cardiac development in axolotl mesodermal explants," *Development* 112:1095-1101 (1991).
Narita, N. et al., "Cardiomyocyte differentiation by GATA-4-deficient embryonic stem cells," *Development* 122:3755-64 (1996).
O'Shea, K., "Embryonic stem cell models of development," *Anatomical Record (New Anat)* 257(1):32-41 (1999).
Odorico, J. et al., "Multilineage differentiation from human embryonic stem cell lines," *Stem Cells* 19:193-204 (2001).
Oh, H. et al., "Cardiac progenitor cells from adult myocardium: Homing, differentiation, and fusion after infarction," *PNAS* 100(21):12313-18 (2003).
Olson, E. & Srivastava, D., "Molecular pathways controlling heart development," *Science* 272:671-75 (1996).
Qin, L. et al., "Gene transfer of transforming growth factor-β1 prolongs murine cardiac allograft survival by inhibiting cell-mediated immunity," *Human Gene Therapy* 7:1981-88 (1996).
Reubinoff, B. et al., "Embryonic stem cell lines from human blastocysts: somatic differentiation in vitro," *Nature Biotech.* 18:399-404 (2000).
Satin, J. et al., "Mechanism of spontaneous excitability in human embryonic stem cell derived cardiomyocytes," *J. Physiol.* 559(2):479-96 (2004).
Scalia, P. et al., "Regulation of the Akt/Glycogen synthase kinase-3 axis by insulin-like growth factor-II via activation of the human insulin receptor isoform-A," *J. Cell. Biochem.* 82:610-18 (2001).
Schlange, T. et al., "BMP2 is required for early heart development during a distinct time period," *Mech. Dev.* 91:259-70 (2000).
Schneider, V. & Mercola, M., "Wnt antagonism initiates cardiogenesis in *Xenopus laevis*," *Genes Dev.* 15:304-15 (2001).
Schuldiner, M. et al., "Effects of eight growth factors on the differentiation of cells derived from human embryonic stem cells," *PNAS* 97(21):11307-12 (2000).
Schultheiss, T. et al., "A role for bone morphogenetic proteins in the induction of cardiac myogenesis," *Genes Dev.* 11:451-62 (1997).
Schultheiss, T. et al., "Induction of avian cardiac myogenesis by anterior endoderm," *Development* 121:4203-14 (1995).
Shamblott, M. et al., "Derivation of pluripotent stem cells from cultured human primordial germ cells," *Proc. Natl. Acad. Sci. USA* 95:13726-31 (1998).
Shi, Y. et al., "BMP signaling is required for heart formation in vertebrates," *Dev. Biol.* 224:22637 (2000).
Skerjanc, I. et al., "Myocyte enhancer factor 2C and Nkx2-5 up-regulate each other's expression and initiate cardiomygenesis in P19 cells," *J. Biol. Chem.* 273(52):34904-19 (1998).
Sugi, Y. & Lough, J., "Activin-A and FGF-2 mimic the inductive effects of anterior endoderm on terminal cardiac myogenesis in Vitro," *Dev. Biology* 168:567-74 (1995).
Symes, K. et al., "Morphological differences in *Xenopus* embryonic mesodermal cells are specified as an early response to distinct threshold concentrations of activin," *Development* 120:2339-46 (1994).
Thomson, J. et al., "Embryonic stem cell lines derived from human blastocysts," *Science* 282:1145-7 (1998).
Van Laake, L. et al., "Cardiomyocytes derived from stem cells," *Ann. Med.* 37:499-512 (2005).
Vélez, C. et al., "Modulation of contractile protein troponin-T in chick myocardial cells by basic fibroblast growth factor and platelet-derived growth factor during development," *J. Cardiovasc. Pharmacol.* 24:906-13 (1994).
Walters, M. et al., "Bone morphogenetic protein function is required for terminal differentiation of the heart but not for early expression of cardiac marker genes," *Mech. Dev.* 100:263-73 (2001).

Wobus, A. et al., "Development of cardiomyocytes expressing cardiac-specific genes, action potentials, and ionic channels during embryonic stem cell-derived cardiogenesis," *Ann. N.Y. Acad. Sci.* 752:460-9 (1995).
Wobus, A. et al., "In Vitro cellular models for cardiac development and pharmacotoxicolgy," *Toxic. In Vitro* 9:477-88 (1995).
Wobus, A. et al., "Retinoic acid accelerates embryonic stem cell-derived cardiac differentiation and enhances development of ventricular cardiomyocytes," *J. Mol. Cell Cardiol.* 29:1525-39 (1997).
Xiao, Y.-F., "Cardiac application of embryonic stem cells," *Acta Physiologica Sinica* 55(5):493-504 (2003).
Xu, C. et al., "Characterization and enrichment of cardiomyocytes derived from human embryonic stem cells," *Circ. Res.* 91(6):501-8 (2002).
Xu, C. et al., "Feeder-free growth of undifferentiated human embryonic stem cells," *Nat. Biotech.* 19(10):971-4 (2001).
Xu, C. et al., "Specific arrest of cardiogenesis in cultured embryonic stem cells lacking Cripto-1," *Dev. Biol.* 196:237-47 (1998).
Xu, C. et al., "Cardiac Bodies: a novel culture method for enrichment of cardiomyocytes derived from human embryonic stem cells," *Stem Cells & Dev.* 15:631-9 (2006).
Yatskievych, T. et al., "Induction of cardiac myogenesis in avian *pregastrula* epiblast: the role of the hypoblast and activin," *Development* 124:2561-70 (1997).
Zandstra, P. et al., "Scalable production of embryonic stem cell-derived cardiomyocytes," *Tissue Engineering* 9(4):767-78 (2003).
Zhu, X. et al., "Evidence that fibroblast growth factors 1 and 4 participate in regulation of cardiogenesis," *Dev. Dynamics* 207:429-38 (1996).
Zingg, J.-M. et al., "Genetic and epigenetic aspects of DNA methylation on genome expression, evolution, mutation and carcinogenesis," *Carcinogenesis* 18(5):869-82 (1997).
Dubus, I. et al., "Contractile protein gene expression in serum-free cultured adult rat cardiac myocytes," *Pflügers Arch.* 423:455-61 (1993).
Khamsi, R. "Market Watch," *Nature* 437:1231 (2005).
Khamsi, R. "Geneticists hail variety show, map of DNA differences will help experts tailor drugs," *Nature*, online, 2 pages (Oct. 26, 2005).
Koide, M. et al., "Atrial natriuretic peptide accelerates proliferation of chick embryonic cardiomyocytes in vitro," *Differentiation* 61:1-11 (1996).
Lim, J. & Bodnar, A., "Proteome analysis of conditioned medium from mouse embryonic fibroblast feeder layers which support the growth of human embryonic stem cells," *Proteomics* 2:1187-203 (2002).
Murrell, W. et al., "On the ontogeny of cardiac gene transcripts," *Mech. Ageing & Dev.* 77:109-26 (1994).
Murry, C. et al., "Muscle cell grafting for the treatment and prevention of heart failure," *J. Cardiac Failure* 8(6):S532-41 (2002).
Nair, P. & Nair, R., "Selective use of calcium chelators enhances the yield of calcium-tolerant myocytes from adult heart," *Indian J. Exp. Biol.* 35(5):451-6, 1 page Abstract (1997).
Pandur, P "What does it take to make a heart?" *Biol. Cell* 97:197-210 (2005).
Rice, N. & Leinwand, L., "Skeletal myosin heavy chain function in cultured lung myofibroblasts," *J. Cell Biol.* 163(1):119-29 (2003).
Strauer, B. et al., "Stem cell therapy in perspective," *Circulation* 107:929-34 (2003).
Takahashi, K. et al., "Taurine renders the cell resistant to ischemia-induced injury induced in cultured neonatal rat cardiomyocytes," *J. Cardiovasc, Pharmacol.* 41:726-33 (2003).
Thomson, J. et al., "Isolation of a primate embryonic stem cell line," *Proc. Natl. Acad. Sci. USA* 92:7844-8 (1995).
Verfaillie, C. et al., "Stem Cells: Hype and Reality," *Hematology Am. Soc. Hematol. Educ. Program*, pp. 369-91 (2002).
Volz, A. et al., "Longevity of adult ventricular rat heart muscle cells in serum-free primary culture," *J. Mol. Cell Cardiol.* 23:161-73 (1991).
Goldman, B. et al., "Epidermal growth factor promotes a cardiomyoblastic phenotype in human fetal cardiac myocytes," *Exp. Cell Res.* 228:237-45 (1996).

(56) References Cited

OTHER PUBLICATIONS

Piao, S. et al., "A simplified method for identification of human cardiac myosin heavy-chain isoforms," *Biotechnol. Appl. Biochem.* 37:27-30 (2003).

Czyz, J. et al., "Potential of embryonic and adult stem cells in vitro," *Biol. Chem.* 384:1391-409 (2003).

Gerecht-Nir, S. et al., "Vascular gene expression and phenotypic correlation during differentiation of human embryonic stem cells," *Dev. Dyn.* 232:487-97 (2005).

Oh, S. et al., "Human embryonic stem cells: technological challenges towards therapy," *Clin. Exp. Pharmacol. Physiol.* 33:489-95 (2006).

Ginis, I. et al., "Differences between human and mouse embryonic stem cells," *Dev. Biol.* 269:360-80 (2004).

Pending claims for U.S. Appl. No. 10/805,099, dated Nov. 25, 2008, 2 pages.

Pending claims for U.S. Appl. No. 11/040,691, dated Jul. 8, 2009, 3 pages.

Pending claims for U.S. Appl. No. 12/210,779, dated Sep. 15, 2008, 2 pages.

Pending claims for U.S. Appl. No. 12/234,916, dated Aug. 27, 2009, 3 pages.

Roy, N. et al., "Identification, isolation, and promoter-defined separation of mitotic oligodendrocyte progenitor cells from the adult human subcortical white matter", *J. Neurosci*, 19, (1999),pp. 9986-9995.

Ruffini, F. et al., "Distinctive properties of human adult brain-derived myelin cells", *Am. J. Pathol.* 165, (2004),pp. 2167-2175.

Verlinsky, Y. et al., "Preimplantation diagnosis for Fanconi anemia combined with HLA mapping", *JAMA* 285(24), (2001),pp. 3130-3133.

Morali, O. et al., "IGF-II promotes mesoderm formation", *Dev. Biol.* 227, (2000),pp. 133-145.

Fukuda, K., "Generation of cardiomyocyte from bone marrow stromal cells", *Blood, Immunity, Tumor* 5(4) (2000), pp. 35-38.

"Stem Cells: Scientific Progress and Future Research Directions", *Dept. Health & Human Svcs. Chapter* 1 (2001), pp. 1-4.

Xu, C., "Human embryonic stem cell-derived cardiomyocytes can be maintained in defined medium without serum", *Stem Cells Dev.* 15 (2006), pp. 931-941.

Singh, A. et al., "Chibby, an antagonist of the Wnt/Beta-catenin pathway, facilitates cardiomyocyte differentiation of murine embryonic stem cells", Circulation 115, (2007),pp. 617-626.

Wobus, A. et al., "Pluripotent mouse embryonic stem cells are able to differentiate into cardiomyocytes expressing chronotropic responses to adrenergic and cholinergic agents and Ca2+ channel blockers", *Differentiation* 48, (1991),pp. 173-182.

Gehlsen, K. et al., "Inhibition of in vitro tumor cell invasion by Arg-Gly-Asp-containing synthetic peptides", *J. Cell. Biol.* 106(3), erratum in J Cell Biol Jun. 1989;108(6):following 2546,(1988),pp. 925-930.

Izumi, M. et al., "The polymorphism and functional specificity of bone morphogentic protein (BMP)", *The Shikwa Gakuho* 102, Abstract in English,(2002),pp. 764-771.

Laflamme, M. et al., "Cardiomyocytes derived from human embryonic stem cells in pro-survival factors enhance funtion of infarcted rat hearts", *Nature Biotechnol* 25, (2007),pp. 1015-1024.

Li, R. et al., "Human pediatric and adult ventricular cardiomyocytes in culture: assessment of phenotypic changes with passaging", *Cardiovasc. Res.* 32, (1996),pp. 362-373.

Rifkin, D. et al., "Bone matrix to growth factors: location, location, location", *J. Cell. Biol.* 190(6), (2010),pp. 949-951.

Xu, X. et al., "Activin, BMP and FGF pathways cooperate to promote endoderm and pancreatic lineage cell differentiation from human embryonic stem cells", *Mech. Dev.* 128, (2011),pp. 412-427.

\* cited by examiner

DIFFERENTIATION OF PRIMATE PLURIPOTENT STEM CELLS TO CARDIOMYOCYTE-LINEAGE CELLS

REFERENCE TO RELATED APPLICATIONS

This application claims priority to U.S. Ser. No. 60/693,141, filed Jun. 22, 2005.

FIELD OF THE INVENTION

This invention relates to the field of in-vitro differentiation of primate pluripotent stem cells into cardiomyocyte-lineage cells.

BACKGROUND

A central challenge for research in regenerative medicine is to develop cell compositions that can help reconstitute cardiac function. It is estimated that nearly one in five men and women have some form of cardiovascular disease (National Health and Nutrition Examination Survey III, 1988-94, Center of Disease Control and the American Heart Association). Widespread conditions include coronary heart disease (5% of the population), congenital cardiovascular defects (0.5%), and congestive heart failure (3%). The pharmaceutical arts have produced small molecule drugs and biological compounds that can help limit the damage that occurs as a result of heart disease, but there is nothing commercially available to help regenerate the damaged tissue.

With the objective of developing a cell population capable of cardiac regeneration, research has been conducted on several different fronts. Clinical trials are underway at several centers to test the use of autologous bone marrow derived cells for therapy after myocardial infarction (Perin et al., Circulation 107:2294, 2003; Strauer et al., Circulation 106:1913, 2002; Zeiher et al., Circulation 106:3009, 2002; Tse et al., Lancet 361:47, 2003; Starnm et al., Lancet 3661:45, 2003). It has been hypothesized that the cells may have a cleansing function to improve blood perfusion of the heart tissue. Clinical trials are also underway to test the use of autologous skeletal muscle myoblasts for heart therapy (Menasche et al., J. Am. Coll. Cardiol. 41:1078, 2003; Pagani et al., J. Am. Coll. Cardiol. 41:879, 2003; Hagege et al., Lancet 361:491, 2003). However, it is unclear if the contraction of striatal muscle cells can coordinate adequately with cardiac rhythm.

A more direct approach would be to use cells that are already committed to be functional cardiomyocytes. Syngeneic neonatal or postnatal cardiac cells have been used in animal models to repair damage resulting from permanent coronary occlusion (Reffelmann et al., J. Mol. Cell Cardiol. 35:607, 2003; Yao et al., J. Molec. Cell. Cardiol. 35:607, 2003). Accordingly, if such cells were available for human therapy, they could be very effective for the treatment of ischemic heart disease. In addition, cardiomyocyte cells can be used for screening compounds such as pharmaceuticals.

BRIEF SUMMARY OF THE INVENTION

The present invention provides methods of obtaining cardiomyocyte-lineage cells from primate pluripotent stem cells. Cardiomyocyte-lineage cells have many possible uses, including, but not limited to, screening of potential pharmaceuticals, screening for cytotoxic chemicals, and therapeutic applications such as in vivo repair of damaged or diseased hearts.

In certain embodiments of the invention, the methods of obtaining cardiomyocyte-lineage cells from primate pluripotent stem cells comprise in the following order: culturing the primate pluripotent stem cells in the presence of an Activin but in the absence of a BMP; subsequently culturing the cells in the presence of a BMP; and harvesting the resulting harvested cells from the culture.

The present invention also provides methods of obtaining enriched populations of cardiomyocyte-lineage cells. In certain embodiments, those methods comprise in the following order: culturing the primate pluripotent stem cells in the presence of an Activin but in the absence of a BMP; subsequently culturing the cells in the presence of a BMP; harvesting the cells from the culture; and enriching the harvested cell population for cardiomyocyte-lineage cells. In certain embodiments, those methods comprise in the following order: culturing the primate pluripotent stem cells in a serum-free medium in the presence of Activin A but in the absence of a BMP for about one day; subsequently culturing the cells in a serum-free medium in the presence of BMP-4 or BMP-2 in the absence of an Activin for about four days; harvesting the cells from the culture; and enriching the harvested cell population for cardiomyocyte-lineage cells.

In certain embodiments of the invention, the cells are attached to a solid surface during the culturing steps. In certain embodiments, the cells are allowed to form an embryoid body during the culturing step with the BMP. In certain embodiments, the cells are cultured in a single-cell suspension during the Activin and/or BMP culture steps.

In certain embodiments, the cells are cultured for one day or more in the presence of the Activin. In certain embodiments, the cells are cultured for four days or more in the presence of the BMP. In certain embodiments, the Activin is Activin A. In certain embodiments, the BMP is BMP-4 or BMP-2.

In certain embodiments, the cells are cultured for an additional time period after the BMP culture step without the presence of an Activin or a BMP. In certain of those embodiments, that additional culture step is two weeks or longer. In certain of those embodiments, an IGF is included in the culture step. In certain of those embodiments, the IGF is IGF-1.

In certain embodiments of the invention, the cell population that results from the differentiation protocol is enriched for cardiomyocyte-lineage cells. In certain of those embodiments, a Percoll gradient is used to enrich the proportion of cardiomyocyte-lineage cells.

In certain embodiments of the invention, the harvested cells are at least 10% positive for α-myosin heavy chain (αMHC). In certain embodiments of the invention, the harvested cells are at least 10% cardiac troponin I (cTnI) positive). In certain embodiments of the invention, the harvested cells are at least 25% cardiac troponin I (cTnI) positive).

In certain embodiments of the invention, cardiac bodies are formed to enrich and/or expand the population of cardiomyocyte-lineage cells. In certain of those embodiments, the methods further comprise separating cells in the enriched cell population that are present as single cells from cells that are present as clusters; resuspending the cells present as clusters in nutrient medium; reculturing the resuspended cells in the nutrient medium; and collecting and washing the recultured cells.

The invention also provides for population of cardiomyocyte-lineage cells differentiated from primate pluripotent stem cells according to the methods of the invention. The invention also provides a plurality of cell populations cultured during production of cardiomyocyte-lineage cells from human blastocyst cells, comprising undifferentiated cells from a line of primate pluripotent stem cells obtained from a human blastocyst; and a population of cardiomyocyte-lineage cells differentiated from said primate pluripotent stem cell line according to the methods of the invention.

In certain embodiments of the invention, the differentiation of primate pluripotent stem cells to cardiomyocyte-lineage cells occurs in a serum-free medium. In certain embodiments of the invention, the differentiation of primate pluripotent stem cells to cardiomyocyte-lineage cells occurs in a medium that contains less than 0.5% serum. In certain embodiments of the invention, the differentiation of primate pluripotent stem cells to cardiomyocyte-lineage cells occurs in a medium that contains less than 1% serum. In certain embodiments of the invention, the differentiation of primate pluripotent stem cells to cardiomyocyte-lineage cells occurs in a medium that contains less than 5% serum.

In certain embodiments of the invention, the cells are adhered to a substrate that comprises s one or more of gelatin, Matrigel, laminin, fibronectin, and/or vitronectin during the differentiation of primate pluripotent stem cells to cardiomyocyte-lineage cells.

In certain embodiments of the invention, the primate pluripotent stem cells are cultured in MEM-CM plus bFGF for one to seven days before the Activin culture step. In certain embodiments, the primate pluripotent stem cells are cultured in MEM-CM plus bFGF for about six days before the Activin culture step.

In certain embodiments, the medium RPMI plus 1× B27 is used when culturing the cells in the presence of an Activin. In certain embodiments, the medium RPMI plus 1× B27 is used when culturing the cells in the presence of an a BMP. In certain embodiments, the medium RPMI plus N2 is used when culturing the cells in the presence of an Activin. In certain embodiments, the medium RPMI plus N2 is used when culturing the cells in the presence of a BMP.

DEFINITIONS

Figure 1A:
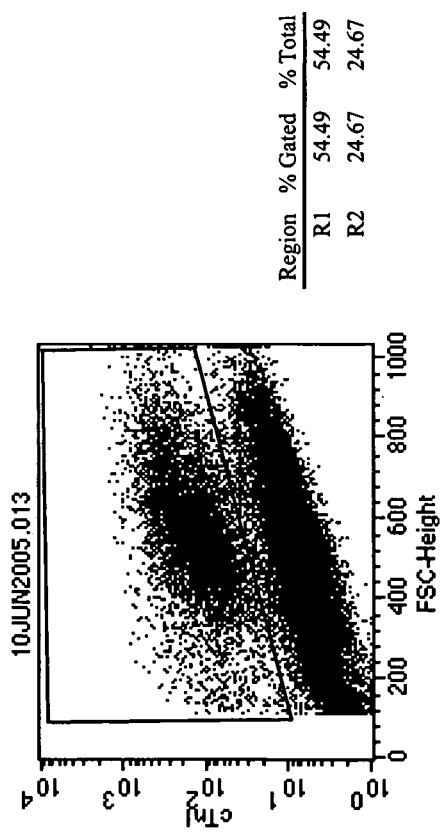
FIG. 1—H7 cells were plated onto wells coated with gelatin and FBS and subsequently differentiated according to the method described in Example 1. On day 24 after the original addition of activin, cultures were dissociated with trypsin-EDTA, fixed, permeablized, and stained with an antibody against cardic troponin I. Prior to fixation, cells were incubated with EMA to distinguish live cells (cells excluding EMA) from dead cells (cells incorporating EMA). Samples were analyzed on a FACScalibur and dead cells were excluded from the analysis. In this experiment, approximately 54% of the cells survived the trypsin dissociation; of these live cells, 24-27% were cardiomyocytes as determined by labeling with the cardiac troponin I-specific antibody. Two different gating methods were used in the 2 panels (FIG. 1A: histogram- and FIG. 1B: scatter-plot based); the percentage of cardiomyocytes was similar by either method.

The term "cardiomyocyte-lineage cells" refers generally to both cardiomyocyte precursor cells and mature cardiomyocytes. Reference to cardiomyocyte-lineage cells, precursors, or cardiomyocytes in this disclosure can be taken to apply equally to cells at any stage of cardiomyocyte ontogeny without restriction, as defined above, unless otherwise specified. As described below, cardiomyocyte-lineage cells may have one or more markers (sometimes at least 3 or 5 markers) from the following list: cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

The term "embryoid bodies" refers to heterogeneous clusters comprising differentiated and partly differentiated cells that appear when primate pluripotent stem cells are allowed to differentiate in a non-specific fashion in suspension cultures or aggregates.

As used herein, "primate pluripotent stem cells" refers to cells that are derived from any kind of embryonic tissue (fetal or pre-fetal tissue) and that have the characteristic of being capable under appropriate conditions of producing progeny of different cell types that are derivatives of all of the 3 germinal layers (endoderm, mesoderm, and ectoderm), according to a standard art-accepted test such as the ability to form a teratoma in 8-12 week old SCID mice or the ability to form identifiable cells of all three germ layers in tissue culture. Included in the definition of primate pluripotent stem cells are embryonic cells of various types, exemplified by human embryonic stem (hES) cells, (see, e.g., Thomson et al. (Science 282:1145, 1998)) and human embryonic germ (hEG) cells (see, e.g., Shamblott et al., Proc. Natl. Acad. Sci. USA 95:13726, 1998); embryonic stem cells from other primates, such as Rhesus stem cells (see, e.g., Thomson et al., Proc. Natl. Acad. Sci. USA 92:7844, 1995), marmoset stem cells (see, e.g., Thomson et al., Biol. Reprod. 55:254, 1996).

As used herein, "undifferentiated primate pluripotent stem cells" refers to a cell culture where a substantial proportion of primate pluripotent stem cells and their derivatives in the population display morphological characteristics of undifferentiated cells. It is understood that colonies of undifferentiated cells within the population will often be surrounded by neighboring cells that are partly differentiated.

As used herein, "embryonic stem cell" refers to pluripotent stem cells that are derived from a human embryo at the blastocyst stage, or before substantial differentiation of the cells into the three germ layers. Except where explicitly required otherwise, the term includes primary tissue and established lines that bear phenotypic characteristics of hES cells, and progeny of such lines that still have the capacity of producing progeny of each of the three germ layers. Prototype "human Embryonic Stem cells" (hES cells) are described by Thomson et al. (Science 282:1145, 1998; U.S. Pat. No. 6,200, 806).

As used herein, "Activin" refers to a polypeptide growth factor that is a member of the transforming growth factor-β (TGF-β) superfamily. Currently there are four know Activins—A, AB, B, and C.

As used herein, "Bone Morphogenetic Protein (BMP)" refers to a polypeptide growth factor of the TGF-β superfamily. There are currently about 20 known members in the BMP family. For the purposes of this application, the term "BMP" does not include BMP-1. As used herein, "enrich" refers to increasing the level of a component in a mixture. For example, in certain embodiments of the present invention, a given cell population may be enriched by increasing the proportion of cardiomyocyte-lineage cells in that population.

As used herein, "cardiac body" refers to a cluster of primate pluripotent stem cell-derived cells in suspension, bearing two or more characteristics of human cardiomyocyte-lineage cells.

As used herein, "direct differentiation" refers to a process for differentiating primate pluripotent stem cells into progeny that are enriched for cells of a particular tissue type without forming embryoid bodies as an intermediate. To clarify, the term direct differentiation encompasses processes in which a small number of cell aggregates form inadvertently.

As used herein, "genetically altered", "transfected", or "genetically transformed" refer to a process where a polynucleotide has been transferred into a cell by any suitable means of artificial manipulation, or where the cell is a progeny of the originally altered cell and has inherited the polynucleotide. The polynucleotide will often comprise a transcribable sequence encoding a protein of interest, which enables the cell to express the protein at an elevated level or may comprise a sequence encoding a molecule such as siRNA or antisense RNA that affects the expression of a protein (either expressed by the unmodified cell or as the result of the introduction of another polynucleotide sequence) without itself encoding a protein. The genetic alteration is said to be "inheritable" if progeny of the altered cell have the same alteration.

As used herein, "serum-free" refers to a condition where the referenced composition contains no added serum.

As used herein, "feeder cells" refers to cells of a different tissue type, and typically a different genome, that may act to promote proliferation and/or control differentiation of cells they are cocultured with. For example, undifferentiated primate pluripotent stem cells can be cocultured with feeder cells that help maintain the undifferentiated state, while primate pluripotent stem cells in the process of being differentiated can be cocultured with feeders that direct differentiation towards a particular tissue type (e.g., cardiomyocyte-lineage cells).

As used herein, "feeder-free" refers to a condition where the referenced composition contains no added feeder cells. To clarify, the term feeder-free encompasses, inter alia, situations where primate pluripotent stem cells are passaged from a culture with feeders into a culture without added feeders even if some of the feeders from the first culture are present in the second culture.

As used herein, "culturing" refers to the process of maintaining and/or expanding cells in vitro.

As used herein, "same genome" refers to the genomes of a primate pluripotent stem cell and a differentiated cell derived from that primate pluripotent stem cell and means that the chromosomal DNA will be over 90% identical between the primate pluripotent stem cell and the derived cell as determined by Restriction Fragment Length Polymorphism ("RFLP") or SNP analysis. Even if the primate pluripotent stem cell or the derived cell has been genetically altered, those cells will be considered to have the same genome as the cell from which it was derived or the cell derived from it, since all non-manipulated genetic elements are preserved.

As used herein, "Matrigel" refers to BD Matrigel™ Basement Membrane Matrix, which is a commercial preparation of basement membrane produced by Engelbreth-Holm-Swarm tumor cells and containing extracellular matrix components such as laminin. Matrigel is available commercially through Becton, Dickinson and Company (Franklin Lakes, N.J.).

As used herein, "RPMI" refers to RPMI Medium 1640 (Invitrogen, Carlsbad, Calif.).

DETAILED DESCRIPTION OF THE INVENTION

General Techniques—For further elaboration of general techniques useful in the practice of this invention, the practitioner can refer to standard textbooks and reviews in cell biology, tissue culture, embryology, and cardiophysiology.

With respect to tissue and cell culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998; and R. I. Freshney, Culture of Animal Cells, Wiley-Liss, New York, 2000). With respect to the culture of heart cells, standard references include *The Heart Cell in Culture* (A. Pinson ed., CRC Press 1987), *Isolated Adult Cardiomyocytes* (Vols. I & II, Piper & Isenberg eds., CRC Press 1989), and *Heart Development* (Harvey & Rosenthal, Academic Press 1998). General methods in molecular and cellular biochemistry can be found in such standard textbooks as *Short Protocols in Molecular Biology, 4th* Ed.; *Immunology Methods Manual* (I. Lefkovits ed., Academic Press 1997); and *Cell and Tissue Culture: Laboratory Procedures in Biotechnology* (Doyle & Griffiths, John Wiley & Sons 1998).

Primate Pluripotent Stem Cells

The present invention provides methods for differentiating primate pluripotent stem cells into cardiomyocyte-lineage cells. Primate pluripotent stem cells that may be used in the methods of the invention include, but are not limited to, embryonic stem cells. Embryonic stem cells can be isolated from blastocysts of primate species (U.S. Pat. No. 5,843,780; Thomson et al., Proc. Natl. Acad. Sci. USA 92:7844, 1995). Human embryonic stem (hES) cells can be prepared from human blastocyst cells using, for example, the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Other primate pluripotent stem cell types include, but are not limited to, primitive ectoderm-like (EPL) cells, outlined in WO 01/51610 (Bresagen) and human embryonic germ (hEG) cells (Shamblott et al., Proc. Natl. Acad. Sci. USA 95:13726, 1998).

Embryonic stem cells used in the invention may be chosen from embryonic stem cell lines or may be obtained directly from primary embryonic tissue. A large number of embryonic stem cell lines have been established including, but not limited to, H1, H7, H9, H13 or H14 (reference Thompson); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6

(from University of California at San Francisco); I3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471): 1636-41, 2005).

In certain embodiments, primate pluripotent stem cells used in the present invention may have been derived in a feeder-free manner (see, e.g., Klimanskaya et al., Lancet, 365(9471):1636-41 (2005)).

Primate Pluripotent Stem Cell Culture

Primate pluripotent stem cells may be cultured using a variety of substrates, media, and other supplements and factors known in the art. Primate pluripotent stem cells can be propagated continuously in culture, using culture conditions that promote proliferation while inhibiting differentiation. Exemplary medium is made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM β-mercaptoethanol.

In certain embodiments, primate pluripotent stem cells are cultured on a layer of feeder cells, typically fibroblasts derived from embryonic or fetal tissue (Thomson et al., Science 282:1145, 1998). In certain embodiments, those feeder cells are from human or mouse. Human feeder cells can be isolated from various human tissues or derived by differentiation of human embryonic stem cells into fibroblast cells (see, e.g., WO 01/51616) In certain embodiments, human feeder cells that may be used include, but are not limited to, placental fibroblasts (see, e.g., Genbacev et al., Fertil. Steril. 83(5):1517-29, 2005), fallopian tube epithelial cells (see, e.g., Richards et al., Nat. Biotechnol., 20:933-36, 2002), foreskin fibroblasts (see, e.g., Amit et al., Biol. Reprod. 68:2150-56, 2003), uterine endometrial cells (see, e.g., Lee et al., Biol. Reprod. 72(1):42-49, 2005)

In certain embodiments, embryonic stem cells may be maintained in an undifferentiated state without added feeder cells (see, e.g., Rosler et al., Dev. Dynam. 229:259-274, 2004). Feeder-free cultures are typically supported by a nutrient medium containing factors that promote proliferation of the cells without differentiation (see, e.g., U.S. Pat. No. 6,800, 480). In certain embodiments, such factors may be introduced into the medium by culturing the medium with cells secreting such factors, such as irradiated (~4,000 rad) primary mouse embryonic fibroblasts, telomerized mouse fibroblasts, or fibroblast-like cells derived from primate pluripotent stem cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days is supplemented with further bFGF, and used to support primate pluripotent stem cell culture for 1-2 days (see.e.g., WO 01/51616; Xu et al., Nat. Biotechnol. 19:971, 2001).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Biowhittaker) or QBSF™-60 (Quality Biological Inc.), supplemented with bFGF at 40-80 ng/mL, and optionally containing stem cell factor (15 ng/mL), or Flt3 ligand (75 ng/mL) (see, e.g., Xu et al., Stem Cells 23(3):315-23, 2005). These medium formulations have the advantage of supporting cell growth at 2-3 times the rate in other systems (see, e.g., WO 03/020920).

For example, the primate pluripotent stem cells are plated at >15,000 cells $cm^{-2}$ (optimally 90,000 $cm^{-2}$ to 170,000 $cm^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS or by simply detaching the desired cells from the plate mechanically, such as by scraping or isolation with a fine pipet. After washing from the culture vessel, the cells are plated into a new culture without further dispersal. In a further illustration, confluent human embryonic stem cells cultured in the absence of feeders are removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells $cm^{-2}$ to promote survival and limit differentiation.

Under the microscope, primate pluripotent stem cells appear with high nuclear/cytoplasmic ratios, prominent nucleoli, and compact colony formation with poorly discernable cell junctions. Primate primate pluripotent stem cells typically express the stage-specific embryonic antigens (SSEA) 3 and 4, and markers detectable using antibodies designated Tra-1-60 and Tra-1-81. Undifferentiated human embryonic stem cells also typically express the transcription factor Oct-3/4, Cripto, gastrin-releasing peptide (GRP) receptor, podocalyxin-like protein (PODXL), and human telomerase reverse transcriptase (hTERT) (US 2003/0224411 A1), as detected by RT-PCR.

Differentiation of Primate Pluripotent Stem Cells to Cardiomyocyte-Lineage Cells The present invention provides, inter alia, methods for differentiating primate pluripotent stem cells into cardiomyocyte-lineage cells by the sequential culturing of the primate pluripotent stem cells first in the presence of an Activin with subsequent culturing in the presence of a BMP. Although the BMP is excluded during the culturing step with Activin, the Activin may optionally be included during the subsequent culturing step with the BMP.

In certain embodiments, Activin is included in the culture medium at a concentration between 10 ng/ml and 200 ng/ml, or between 25 ng/ml and 100 ng/ml, or between 50 ng/ml and 100 ng/ml. In certain embodiments, Activin is included in the culture medium at a concentration below 10 ng/ml or above 200 ng/ml.

In certain embodiments, the BMP is included in the culture medium at a concentration between 10 ng/ml and 200 ng/ml, or between 25 ng/ml and 100 ng/ml, or between 50 ng/ml and 100 ng/ml. In certain embodiments, the BMP is included in the culture medium at a concentration below 10 ng/ml or above 200 ng/ml.

In certain embodiments, the Activin used in the differentiation is Activin A, Activin B, Activin AB, or Activin C. In certain embodiments, more than one Activin may be used. In certain embodiments, other TGFβ superfamily members such as TGFβ, nodal, or lefty may be substituted instead of or in addition to the Activin in the methods of the present invention.

In certain embodiments, the BMP used in the differentiation is BMP-2, BMP-4, or BMP-7. In certain embodiments, the BMP is a BMP other than BMP-2, BMP-4 or BMP-7 (excluding BMP-1). In certain embodiments, more than one BMP may be used.

In certain embodiments, the differentiating cells are cultured in the absence of both Activin and BMP after the BMP step. In certain of those embodiments, an IGF is included in that culture step. In certain of those embodiments, the IGF is included at a concentration between 10 ng/ml and 500 ng/ml; or between 25 ng/ml and 100 ng/ml; or between 50 ng/ml and 100 ng/ml. In certain embodiments, the IGF is included at concentrations less than 10 ng/ml or more than 500 ng/ml. The IGF may be IGF-1 or IGF-2. In certain embodiments, insulin may be substituted for the IGF in the methods of the present invention.

During the differentiation of the primate pluripotent stem cells to cardiomyocyte-lineage cells, the cells are cultured in the presence of the Activin, BMP, or IGF for various specified time periods. In certain embodiments, the culture step with Activin is between 12 hours and 36 hours in length, or between 12 hours and 2 days in length, or between 6 hours and 4 days in length, or between 4 hours and 5 days in length. In certain embodiments, the culture step with Activin is longer than 5 days.

In certain embodiments, the culture step with the BMP is between 3 days and 5 days in length, or between 2 days and 8 days in length, or between 1 day and 14 days in length. In certain embodiments, the culture step with the BMP is longer than 14 days.

In certain embodiments, the culture step with the IGF is between 3 days and 5 days in length, or between 2 days and 8 days, or between 1 day and 4 weeks in length. In certain embodiments, the culture step with the IGF is longer than 4 weeks long.

For example, in certain embodiments, human embryonic stem cells plated on Matrigel may be first cultured with 50 ng/ml Activin A in the absence of a BMP for about one day, then cultured with 50 ng/ml BMP-4 in the absence of an Activin for about four days, and then cultured in the presence of 50 ng/ml IGF-1 in the absence of both an Activin and a BMP for two weeks. In certain of those embodiments, the resulting cardiomyocyte-lineage cells are harvested and enriched by Percoll gradient as described in Example 3.

In certain embodiments, the primate pluripotent stem cells may be differentiated into cardiomyocyte-lineage cells by direct differentiation. Differentiation paradigms for primate pluripotent stem cells traditionally involve the deliberate formation of embryoid bodies, which allows cross-talk between different cell types, thought to promote tissue formation in a manner reminiscent of an embryo. However, it is often advantageous to eliminate the need to form embryoid bodies, allowing the differentiation process to be more controlled, and the resulting cell population tends to be more uniform (see, e.g., WO 01/51616; US 2002/0151053 A1).

One of the advantages of the direct differentiation technique is that a serum or serum substitute is not needed to initiate or support the cardiomyocyte differentiation process, as is typical of other methods. Instead, the medium can be formulated so that it contains an artificial nutritional supplement that supports differentiated cells like cardiomyocytes or neurons. Exemplary are B27 supplement, N2 supplement, and G5 supplement (Life Technologies/Gibco). In certain embodiments, supplements comprise nutrients and cofactors like human insulin (500 µg/L), human transferrin (5-10 mg/mL), and selenium (0.5 µg/mL), and may also contain putrescine (1.5 mg/L), biotin (1 µg/L), hydrocortisone (0.4 µg/L), or progesterone (0.6 µg/L), and/or low levels of mitogens like EGF or FGF (1 µg/L). For purposes of commercial scale production and human therapy, elimination of components derived from non-human animals may be advantageous.

In certain embodiments, the culture medium used during the differentiation steps is serum-free. In certain embodiments, the culture medium used during the differentiation steps contains less than 0.25% serum, or less than 0.5% serum, or less than 1.0% serum, or less than 2.0% serum, or less than 5.0% serum, or less than 10% serum.

Notwithstanding the advantages of the direct differentiation method, in certain embodiments of the present invention, the primate pluripotent stem cells may be differentiated by the methods of the present invention into cardiomyocyte-lineage cells through the formation of embryoid bodies at some point in the differentiation protocol except for the Activin culture step. Embryoid bodies can be formed in a variety of ways known in the art.

In certain embodiments, the differentiating cells are cultured on a substrate during the methods of the invention. Substrates that can be used in this invention include, but are not limited to collagen, laminin, fibronectin, vitronectin, hyaluronate poly-L-lysine-coated tissue culture plastic, or Matrigel.

In the practice of the present invention, there are various solid surfaces that may be used in the culturing of cells. Those solid surfaces include, but are not limited to, standard cell culturing plates such as 6-well, 24-well, 96-well, or 144-well plates. Other solid surfaces include, but are not limited to, microcarriers and disk. In certain embodiments, the microcarriers are beads. Those beads come in various forms such as Cytodex Dextran microcarrier beads with positive charge groups to augment cell attachment, gelatin/collagen-coated beads for cell attachment, and macroporous microcarrier beads with different porosities for attachment of cells. The Cytodex dextran, gelatin-coated and the macroporous microcarrier beads are commercially available (Sigma-Aldrich, St. Loius, Mo. or Solohill Engineering Inc., Ann Arbor, Mich.). In certain embodiments, the beads are 90-200 µm in size with an area of 350-500 $cm^2$. Beads may be composed of a variety of materials such as, but not limited to, glass or plastic. In certain embodiments, disks may be used in stirred-tank bioreactors for attachment of the cells. Disks are sold by companies such as New Brunswick Scientific Co, Inc. (Edison, N.J.). In certain embodiments, the disks are Fibra-cel Disks, which are polyester/polypropylene disks. A gram of these disks provide a surface area of 1200 $cm^2$.

The solid surface may be made of a variety of substances including, but not limited to, glass or plastic such as polystyrene, polyvinylchloride, polycarobnate, polytetrafluorethylene, melinex, or thermanox. In certain embodiments of the invention, the solid surfaces may three-dimensional in shape. Exemplary three-dimensional solid surfaces are described, e.g., in US20050031598.

In certain embodiments, the cells are in a single-cell suspension during the methods of the invention. The single-cell suspension may be performed in various ways including, but not limited to, culture in a spinner flask, in a shaker flask, or in a fermentors. Fermentors that may be used include, but are not limited to, Celligen Plus (New Brunswick Scientific Co, Inc., Edison, N.J.), and the STR or the Stirred-Tank Reactor (Applikon Inc., Foster City, Calif.). In certain embodiments, the bioreactors may be continuously perfused with media or used in a fed-batch mode. Bioreactors come in different sizes like 2.2 L, 5 L, 7.5 L, 14 L or 20 L.

Enriching and Expanding Cardiomyocyte-Lineage Cells

The present invention provides methods for obtaining high purity cardiomyocyte-lineage cell populations without an enrichment step. However, the addition of one or more enrichment steps may produce an even higher purity cardiomyocyte-lineage cell population. Thus, methods of the invention may include steps for enriching and/or expanding cardiomyocyte-lineage cells obtained by the differentiation steps of the invention. Various methods for enriching specific cell types are known in the art and include, but are not limited to, mechanical separation, density separation, cell sorting, magnetic sorting, and genetic selection techniques (for a general discussion of cell separation, see Freshney, Culture of Animal Cells, Wiley-Liss, New York, 2000—Chapter 14). Examples of some of those methodologies are discussed below.

Density Gradients

In certain embodiments, cardiomyocyte-lineage cells are enriched by density gradient separation using density gradient mediums such as, but not limited to, Percoll (see, e.g., Example 3 herein and Xu et al., Circ. Res. 91(6):501-08, 2002), Ficoll (Pharmacia), metrizamide (Nygaard), Redi-Grad (GE Healthcare) and dextran.

Cell Sorting Techniques

Many cell sorting techniques are available for sorting cardiomyocyte-lineage cells from non-cariomyocyte-lineage cells. Those cell sorting techniques include, but are not limited to negative immunoselection and positive immunoselection.

Immunoselection is a generic term that encompasses a variety of techniques in which the specificity of a selection system is conferred by an antibody or an antibody-like molecule such as a lectin or hapten. An example of such specificity is the affinity of an antibody for a specific cell surface antigen. Two general types of immunoselection techniques are practiced. Negative immunoselection involves the elimination of a specific subpopulation of components from a heterogeneous population such as the elimination on non-cardiomyocyte-lineage cells from the cell population that results from the differentiation of primate pluripotent stem cells according to the methods herein. In contrast, positive immunoselection refers to the direct selection and recovery of a specific component, such as the direct selection and recovery of cardiomyocyte-lineage cells from the differentiation of primate pluripotent stem cells according to the methods herein. Various types of immunoselection may be used in the practice of the present invention, including, but not limited to, flow cytometry (FACS), immunomagnetic techniques, antibody columns, immunoprecipitation, and immunopanning.

Cardiac bodies—In certain embodiments, cardiomyocyte-lineage cells may be further expanded or enriched by allowing them to grow in clusters that are referred to as cardiac bodies.

First, a cell population is generated that contains cells with phenotype characteristics of cardiomyocyte-lineage cells, and optionally enriched by density separation or other technique. The cells are then allowed to form clusters, and single cells in the suspension are removed. This can be accomplished by letting the clusters settle, and pipetting out the supernatant containing single cells. Before proceeding, it is sometimes beneficial to break apart the clusters (for example, by brief trypsinization and/or mechanical dispersion). The cells are then cultured in suspension in low adhesion plates in fresh culture medium (exemplified by medium containing fetal bovine serum, serum substitute, or CCT), and allowed to reaggregate into "secondary" cardiac bodies. Culturing then continues with periodic refeeding, as necessary, with cardiomyocyte-lineage cells remaining as clusters of 10 to 5000 cells (typically 50 to 1000 cells) in size.

After a suitable period (typically 1 to 7 days), the cultured cells can be harvested for characterization, or used in drug screening or pharmaceutical manufacture. The purification effect may improve if the cells are taken through further cycles of removing single cells and reculturing the clusters, over a period of 8 days or more. Each cycle can optionally incorporate a step in which the clusters of cells are dispersed into single cells, or smaller cell clusters, to allow for further expansion. Larger clusters may form, either by aggregation of the suspended cells, or by proliferation within the cluster, or both. It is a hypothesis of this invention that cardiomyocyte-lineage cells have a tendency to form such clusters under appropriate conditions, and that the removal of single cells helps eliminate other cell types and increase homogeneity.

The cardiac body technique can be used to expand and/or enrich the cardiomyocytes in the cell population at any time in the differentiation process. As exemplified below, the technique can be used after a previous enrichment step by density separation. Implementation of the technique has benefits that were not anticipated before the making of this invention. In particular, the expression of myosin heavy chain detected by real-time PCR increases 10- to 100-fold when the cells are cultured for a 7 day period. A large proportion of the clusters in the composition exhibit spontaneous contractile activity: usually over 50%, and potentially between about 80% and 100% when processed in the manner described.

Characterization of ES-Differentiated Cardiomyocyte-Lineage Cells

The cardiomyocyte-lineage cells obtained according to the techniques of this invention can be characterized according to a number of phenotypic criteria.

Figure 1B:
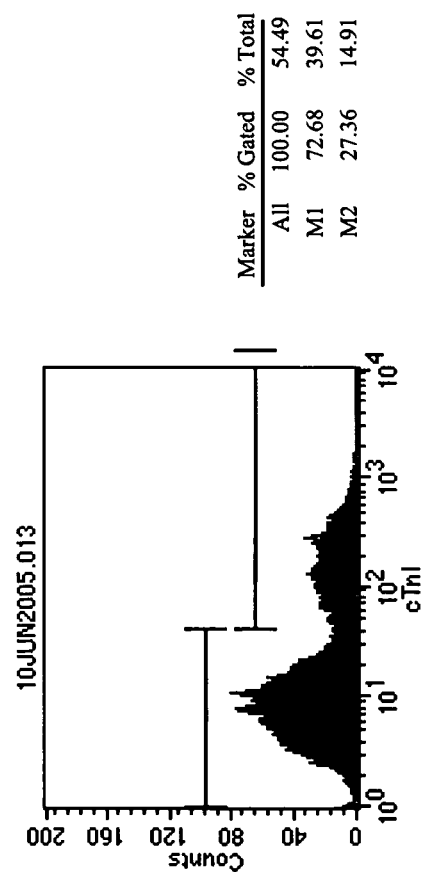

Cardiomyocytes and precursor cells derived from primate pluripotent stem cell lines often have morphological characteristics of cardiomyocytes from other sources. They can be spindle, round, triangular or multi-angular shaped, and they may show striations characteristic of sarcomeric structures detectable by immunostaining (FIG. 1). They may form flattened sheets of cells, or aggregates that stay attached to the substrate or float in suspension, showing typical sarcomeres and atrial granules when examined by electron microscopy.

Figure 2:
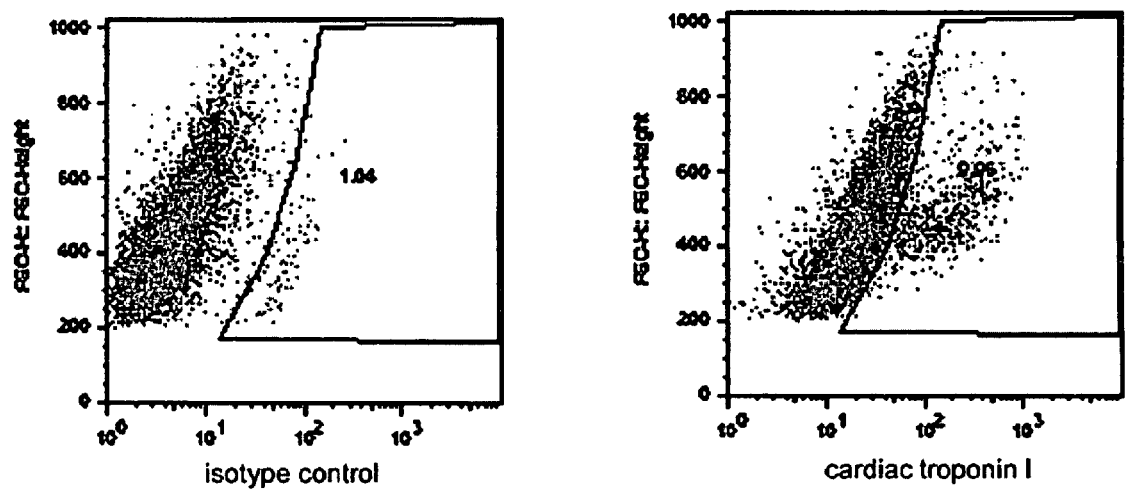
FIG. 2—H7 cells were plated onto wells coated with Matrigel and subsequently differentiated according to the method described in Example 2. On day 21 after the original addition of activin, cultures were dissociated with trypsin-EDTA, fixed, permeablized, and stained with an antibody against cardic troponin I. Prior to fixation, cells were incubated with EMA to distinguish live cells (cells excluding EMA) from dead cells (cells incorporating EMA). Samples were analyzed on a FACScalibur and dead cells were excluded from the analysis. In this experiment, approximately 69% of the cells survived the trypsin dissociation; of these live cells, 8.9% were cardiomyocytes as determined by labeling with the cardiac troponin I-specific antibody.

Under appropriate circumstances, primate pluripotent stem cell-derived cardiomyocytes often show spontaneous periodic contractile activity. This means that when they are cultured in a suitable tissue culture environment with an appropriate $Ca^{++}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between ~6 and 200 contractions per minute, and often between ~20 and ~90 contractions per minute in normal buffer (FIG. 2). Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{++}$ concentration or otherwise interfere with transmembrane transport of $Ca^{++}$ often affect contractile activity. For example, the L-type calcium channel blocker diltiazem inhibits contractile activity in a dose-dependent manner. On the other hand, adrenoceptor agonists like isoprenaline and phenylephrine have a positive chronotropic effect. Further characterization of functional properties of the cell can involve characterizing channels for $Na^+$, $K^+$, and $Ca^{++}$. Electrophysiology can be studied by patch clamp analysis for cardiomyocyte like action potentials. See Igelmund et al., Pflugers Arch. 437:669, 1999; Wobus et al., Ann. N.Y. Acad. Sci. 27:752, 1995; and Doevendans et al., J. Mol. Cell Cardiol. 32:839, 2000.

Cardiomyocyte-lineage cells typically have at least one of the following cardiomyocyte specific markers:

Cardiac troponin I (cTnI), a subunit of troponin complex that provides a calcium-sensitive molecular switch for the regulation of striated muscle contraction Cardiac troponin T (cTnT)

Nkx2.5, a cardiac transcription factor expressed in cardiac mesoderm during early mouse embryonic development, which persists in the developing heart The cells will also typically express at least one (and often at least 3, 5, or more) of the following markers:

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

myosin heavy chain (MHC), particularly the β chain which is cardiac specific

Titin, tropomyosin, α-sarcomeric actinin, and desmin

GATA-4, a transcription factor that is highly expressed in cardiac mesoderm and persists in the developing heart. It regulates many cardiac genes and plays a role in cardiogenesis MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β1-AR)

creatine kinase MB (CK-MB) and myoglobin, which are elevated in serum following myocardial infarction α-cardiac actin, early growth response-I, and cyclin D2.

Tissue-specific markers may be detected using suitable immunological techniques such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products may also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least 2-fold, and preferably more than 10- or 50-fold above that of an undifferentiated primate pluripotent stem cell.

The expression of tissue-specific gene products may also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public databases such as GenBank (URL www.ncbi.nlm.nih.gov:80/entrez). Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of an undifferentiated primate pluripotent stem cell.

Once markers have been identified on the surface of cells of the desired phenotype, they can be used for immunoselection to further enrich the population by techniques such as immunopanning or antibody-mediated fluorescence-activated cell sorting.

Where derived from an established line of primate pluripotent stem cells, the cell populations and isolated cells of this invention can be characterized as having the same genome as the line from which they are derived. This means that the chromosomal DNA will be over 90% identical by RFLP or by SNP analysis between the primate pluripotent stem cells and the cardiac cells, which can be inferred if the cardiac cells are obtained from the undifferentiated line through the course of normal mitotic division. The characteristic that cardiomyocyte-lineage cells are derived from the parent cell population is important in several respects. In particular, the undifferentiated cell population can be used for producing additional cells with a shared genome—either a further batch of cardiac cells, or another cell type that may be useful in therapy—such as a population that can pre-tolerize the patient to the histocompatibility type of the cardiac allograft (US 2002/0086005 A1; WO 03/050251).

Genetic Alteration of Differentiated Cells

The cells of this invention can be made to contain one or more genetic alterations by genetic engineering of the cells either before or after differentiation (US 2002/0168766 A1). For example, the cells can be processed to increase their replication potential by genetically altering the cells to express telomerase reverse transcriptase, either before or after they progress to restricted developmental lineage cells or terminally differentiated cells (US 2003/0022367 A1).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA4, Nkx2.5, and MEF2-C. Production of these factors at the site of administration may facilitate adoption of the functional phenotype, enhance the beneficial effect of the administered cell, or increase proliferation or activity of host cells neighboring the treatment site.

In certain embodiments, it is desirable to genetically alter non-human cardiomyocyte-lineage cells such that the expression of one or more antigens is reduced or eliminated so that the immunogenecity of those cells is reduced. This could be useful, for example, in xenotransplantation of non-human cardiomyocyte-lineage cells into a human.

Uses of ES-Differentiated Cardiomyocyte-Lineage Cells

This invention provides a method to produce large numbers of cells of the cardiomyocyte-lineage. These cell populations can be used for a number of important research, development, and commercial purposes.

Screening

Cardiomyocytes of this invention can be used commercially to screen for factors (such as solvents, small molecule drugs, peptides, oligonucleotides) or environmental conditions (such as culture conditions or manipulation) that affect the characteristics of such cells and their various progeny.

In some applications, primate pluripotent stem cells (undifferentiated or differentiated) are used to screen factors that promote maturation into later-stage cardiomyocyte precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the invention.

The reader is referred generally to the standard textbook *In vitro Methods in Pharmaceutical Research*, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in *In vitro Methods in Pharmaceutical Research*, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

Animal Testing

This invention also provides for the use of cardiomyocytes and their precursors to enhance tissue maintenance or repair of cardiac muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether pluripotent stem derived cells are still present.

This can be performed by administering cells that express a detectable label (such as green fluorescent protein, or β-galactosidase); that have been prelabeled (for example, with BrdU or [$^{31}$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined by assessing the degree of cardiac recuperation that ensues from treatment with a population of cardiomyocyte-lineage cells. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832; Reinecke et al., Circ Res., Epub March 2004). In larger animals, cryoinjury can be effected by placing a 30-50 mm copper disk probe cooled in liquid $N_2$ on the anterior wall of the left ventricle for ~20 min (Chiu et al., Ann. Thorac. Surg. 60:12, 1995). Infarction can be induced by ligating the left main coronary artery (Li et al., J. Clin. Invest. 100:1991, 1997) or by using an ameroid constriction device that gradually swells to occlude an artery. Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

Therapeutic Use in Humans

After adequate testing, differentiated cells of this invention can be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location.

Where desirable, the patient receiving an allograft of cardiomyocyte-lineage cells can be treated to reduce immune rejection of the transplanted cells. Methods contemplated include the administration of traditional immunosuppressive drugs like cyclosporin A (Dunn et al., Drugs 61:1957, 2001), or inducing immunotolerance using a matched population of pluripotent stem derived cells (WO 02/44343; U.S. Pat. No. 6,280,718; WO 03/050251). Another approach is to adapt the cardiomyocyte-lineage cell population to decrease the amount of uric acid produced by the cells upon transplantation into a subject, for example, by treating them with allopurinol. Alternatively or in conjunction, the patient is prepared by administering allopurinol, or an enzyme that metabolizes uric acid, such as urate oxidase (PCT/US04/42917).

Patients suitable for receiving regenerative medicine according to this invention include those having acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, Δpressure/Δtime, patient mobility, and quality of life.

The cardiomyocyte-lineage cells of this invention can be supplied in the form of a pharmaceutical composition, comprising an isotonic excipient prepared under sufficiently sterile conditions for human administration. When the differentiation procedure has involved culturing the cells as cardiac bodies, it may be desirable to disperse the cells using a protease or by gentle mechanical manipulation into a suspension of single cells or smaller clusters. To reduce the risk of cell death upon engraftment, the cells may be treated by heat shock or cultured with ~0.5 U/mL erythropoietin ~24 hours before administration.

For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocyte-lineage cells. Suitable ingredients include matrix proteins that support or promote adhesion of the cardiomyocyte-lineage cells, or complementary cell types, especially endothelial cells.

This invention also includes a reagent system, comprising a set or combination of cells that exist at any time during manufacture, distribution, or use. The cell sets comprise any combination of two or more cell populations described in this disclosure, exemplified but not limited to a type of differentiated pluripotent stem-derived cell (cardiomyocytes, cardiomyocyte precursors, cardiac bodies, and so on), in combination with undifferentiated primate pluripotent stem cells or other differentiated cell types, often sharing the same genome. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of cardiomyocyte-lineage cell function to improve a disease condition or abnormality of the cardiac muscle.

The cells of this invention can be used to prepare a cDNA library relatively uncontaminated with cDNA preferentially expressed in cells from other lineages. For example, cardiomyocyte-lineage cells are collected by centrifugation at 1000 rpm for 5 min, and then mRNA is prepared and reverse transcribed. Expression patterns of the cardiomyocyte-lineage cells can be compared with other cell types by microarray analysis, reviewed generally by Fritz et al Science 288: 316, 2000; "Microarray Biochip Technology", L Shi, www.Gene-Chips.com.

The differentiated cells of this invention can also be used to prepare antibodies that are specific for markers of cardiomyocyte-lineage cells. Polyclonal antibodies can be prepared by injecting a vertebrate animal with cells of this invention in an immunogenic form. Production of monoclonal antibodies is described in such standard references as Harrow & Lane (1988), U.S. Pat. Nos. 4,491,632, 4,472,500 and 4,444,887, and *Methods in Enzymology* 73B:3 (1981).

All publications and patents mentioned in the present application are herein incorporated by reference for any purpose.

Example 1

Three Factor Differentiation on Gelatin/FBS

Preparation of a gelatin/FBS-coated surface: 1 ml/well of 0.5% gelatin solution was added to the wells of a 6-well plate and incubated at 37° C. overnight. The gelatin solution was removed and sufficient 20% FBS-containing medium (e.g., 20% FBS (Sigma) in Knockout DMEM) was added to cover the surface of the wells. The plate incubated at 37° C. for a further 5-6 hours. Prior to addition of the human embryonic stem cells, the medium was removed from well.

Plating undifferentiated human embryonic stem cells for subsequent differentiation: 1 well of a 6 well plate of undifferentiated human embryonic stem cells was dissociated by a) removing medium; b) rinsing well once with PBS; and c) adding 1 ml of 0.25% trypsin/500 mM EDTA solution. The well was incubated at 37° C. for 10 minutes and then triturated ten times with 1 ml pipettor. The well was examined under a microscope to see that the cells were dissociated completely. Two ml of 20% FBS-containing medium (e.g., 20% FBS in Knockout DMEM) was added to inactivate the trypsin. The cells were counted and this number used to plate cells derived from the remaining wells at the desired density.

The medium was removed from the remaining wells. A solution of 20 unit/ml collagenase was added to the wells (1 ml/well). The wells were incubated at 37 degrees for 10 minutes and the collagenase solution removed. 1 ml of MEF-conditioned medium plus 8 ng/ml bFGF was added to the wells. The wells were scraped with a 5 ml pipet until the cells were detached (in small clusters); no further trituration was performed. The cells were diluted to the desired density and plated into 6 well plate prepared as described above (in this case, 670,000 cells in a volume of 5 ml per well; 3 wells were plated). The ES cells were re-fed daily (for cells plated on a Thursday, the feeding on Saturday is usually skipped) by removing the spent medium and replacing it with new MEF-CM plus 8 ng/ml bFGF.

Growth factor treatment: After 6 days of growth as described above, the cells' media was removed and replaced with RPMI plus 1× B27 supplement (Invitrogen) plus 50 ng/ml Activin A (R&D Systems). After 18-24 hours, the medium was removed and replaced with RPMI plus 1× B27 supplement plus 50 ng/ml BMP-4 (R&D Systems). After a total of 4 days in BMP-4-containing medium, the medium was removed and replaced with RPMI plus 1× B27 supplement plus 50 ng/ml IGF-1 (R&D Systems) without the Activin or BMP. The cultures were re-fed every 2-3 days by removing spent medium and replacing it with fresh RPMI plus 1× B27 supplement plus 50 ng/ml IGF-1 without the Activin or BMP.

Numerous beating clusters of cells became evident starting approximately 12 days after the addition of Activin A. On day 24 after the addition of Activin A, cells were counted (9.1 million cells from a total of 3 wells of a 6 well plate), and analyzed by FACS for cardiac troponin I expression by the following procedure:

FACS Analysis—Media was removed from cultures by aspiration. The wells were rinsed once with 5 ml of Calcium/Magnesium-free PBS. One half ml of a solution of 0.25% trypsin/500 mM EDTA was added per well, and the cells were incubated at 37° C. for 20 minutes. The cells were triturated with a pipetor until a single cell suspension was achieved. The trypsin digestion was stopped by the addition of 1 ml of 20% FBS-containing medium (20% FBS in Knockout DMEM). The cell concentration was assessed by counting, and about 500,000 cells were allocated for each staining (EMA, isotype, cTnI, cTnI plus EMA; each in a 15 ml conical tube).

Tubes containing cells were spun in a centrifuge at 400×g for 5 minutes. The medium was aspirated and the cell pellets were resuspended in 1 ml of staining buffer (PBS plus 1% heat inactivated goat serum and 0.1% sodium azide). For EMA staining, cells received EMA to a final concentration of 5 micrograms/ml. These samples were incubated on ice in the dark for 15 minutes, then pelleted as described above. The EMA-treated samples were resuspended in 500 microliters of PBS and exposed to light for 10 minutes. The EMA-treated samples received 500 microliters of 4% paraformaldehyde and were incubated in the dark at room temperature for 15 minutes. Samples that did not receive EMA but that were subsequently stained with antibodies were pelleted as described above, resuspended in 500 microliters of PBS and then received 500 microliters of 4% paraformaldehyde and were incubated in the dark at room temperature for 15 minutes.

All samples were pelleted as described above and resuspended in 100 microliters of PBS. All samples next received 900 microliters of ice-cold 100% methanol and were incubated on ice for 30 minutes. All samples received 1 ml of staining buffer (PBS plus 1% heat inactivated goat serum and 0.1% sodium azide) and pelleted as described above. The supernatant was aspirated and the cells resuspended in blocking buffer (PBS plus 20% normal goat serum and 0.1% sodium azide) at a density of about 500,000 cells/50 microliters. Samples were incubated at 4 degrees for 10-15 minutes. For each stained sample, a 50 microliter aliquot of cells was dispensed into an individual 12×75 mm polystyrene tube. Each sample to be stained received 50 microliters of either cardiac troponin I antibody (Spectral Diagnostics) or isotype control (final amount of antibody per tube was 1.2 micrograms). Samples were incubated at 4 degrees for 30 minutes.

After the addition of 2 ml staining buffer, samples were pelleted as described above. This wash step was repeated. After removal of the $2^{nd}$ wash supernatant, the samples were resuspended in 50 microliters of 5% normal goat serum in PBS containing 0.25 micrograms of the secondary antibody (Molecular Probes goat antimouse IgG labeled with alexa 488). Samples were incubated at 4 degrees for 30 minutes in the dark, and washed with the addition of 2 ml staining buffer and pelleting as described above. The supernatant was decanted and the samples were resuspended in 300 microliters of staining buffer for flow acquisition on a FACScalibur machine.

In this experiment, 54.49% of the total cells were viable after trypsin treatment. Of these viable cells, 24.67-27.36% of the cells were stained with an antibody directed against the cardiomyocyte sarcomeric protein cardiac troponin I. These results are shown in FIG. 1.

Example 2

Three Factor Direct Differentiation on Matrigel-coated surface

An aliquot of growth factor-reduced Matrigel (previously diluted 1:2 with cold Knockout DMEM and stored at −20 degrees). The Matrigel solution was diluted a further 1:15 with cold Knockout DMEM. Empty wells of a 6-well plate were coated with the diluted Matrigel solution at 1 ml/well, and the plate was incubated at room temperature for 4-5 hours. The Matrigel solution was removed, and human ES cells were plated as described below without a pre-rinsing of the wells.

Plating undifferentiated hES cells for subsequent differentiation: 1) The cells in 1 well of the 6 well plate of undifferentiated hES cells were dissociated by a) removing medium; b) rinsing well once with PBS; c) adding 1 ml of 0.05% trypsin/500 mM EDTA solution. The well was incubated in a 37 degree incubator for 10 minutes. The cells were triturated with a pipettor until cells were dissociated completely. 2 ml of 20% FBS-containing medium (e.g., 20% FBS in Knockout DMEM) were added to inactivate trypsin. The cells were counted, and this number used to plate cells derived from the remaining wells at the desired density.

The medium was removed from the remaining wells. A solution of collagenase (200 units/ml) was added at 1 ml/well, and the well incubated at 37° C. for 10 minutes. The collagenase solution was removed, and MEF-conditioned medium plus 8 ng/ml bFGF was added. The well was scraped with a pipet until cells were detached (in small clusters); no further trituration was performed. The cells were diluted to a desired density and plated into a 6-well plate prepared as described above (1.85 million cells in a volume of 5 ml per well). The plated hES cells were fed daily (except not on the second day) by removing the spent medium and replacing it with new MEF-CM plus 8 ng/ml bFGF.

Growth factor treatment: After 6 days of growth as described above, the cells' media was removed and replaced with RPMI plus 1× B27 supplement plus 50 ng/ml Activin A. After 18-24 hours, the medium was removed and replaced with RPMI plus 1× B27 supplement plus 50 ng/ml BMP-4 without the Activin A. After a total of 4 days in the BMP-4-containing medium, the medium was removed and replaced with RPMI plus 1× B27 supplement plus 50 ng/ml IGF-1 without the Activin or BMP. The culture were re-fed every 2-3 days by removing spent medium and replacing it with fresh RPMI plus 1× B27 supplement plus 50 ng/ml IGF-1 without the Activin or BMP.

Beating cells were evident 10-12 days after the addition of the Activin A. On day 21, the cells were counted and analyzed by FACS for cardiac troponin I expression as described below FACS Analysis—Media was removed from cultures by aspiration. The wells were rinsed once with 5 ml of Calcium/Magnesium-free PBS. One ml of a solution of 0.25% trypsin/500 mM EDTA was added per well, and the cells were incubated at 37° C. for 5 minutes. The detached cells in trypsin were transferred to 15 ml conical tubes and incubated at 37° C. for a further 15-20 minutes. The cells were triturated with a pipetor until a single cell suspension was achieved. The trypsin digestion was stopped by the addition of 2 ml of 20% FBS-containing medium (20% FBS in Knockout DMEM). The cell concentration was assessed by counting, and about 500,000 cells were allocated for each staining (EMA, isotype, cTnI, cTnI plus EMA; each in a 15 ml conical tube). Tubes containing cells were spun in a centrifuge at 400×g for 5 minutes. The medium was aspirated and the cell pellets were resuspended in 1 ml of staining buffer (PBS plus 2% heat inactivated fetal calf serum and 0.1% sodium azide). For EMA staining, cells received EMA to a final concentration of 5 micrograms/ml. These samples were incubated on ice in the dark for 15 minutes, then pelleted as described above. The EMA-treated samples were resuspended in 1 ml of PBS and exposed to light for 10 minutes. The EMA-treated samples received 1 ml of 4% paraformaldehyde and were incubated in the dark at room temperature for 15 minutes. Samples that did not receive EMA but that were subsequently stained with antibodies were pelleted as described above, resuspended in 500 microliters of PBS and then received 500 microliters of 4% paraformaldehyde and were incubated in the dark at room temperature for 15 minutes. All samples were pelleted as described above and resuspended in 100 microliters of PBS.

All samples next received 900 microliters of ice-cold 100% methanol and were incubated on ice for 30 minutes. All samples received 1 ml of staining buffer (PBS plus 2% heat inactivated fetal calf serum and 0.2 microgram/0.5×10⁶ cells of rat antimouse Fc block (BD) and pelleted as described above. The supernatant was aspirated and the cells resuspended in blocking buffer (PBS plus 20% normal goat serum and 0.1% sodium azide) at a density of about 500,000 cells/100 microliters. Samples were incubated at 4 degrees for 10-15 minutes. For each stained sample, a 100 microliter aliquot of cells was dispensed into an individual 12×75 mm polystyrene tube. Each sample to be stained received 20 microliters of either cardiac troponin I antibody (Spectral Diagnostics) or isotype control (final amount of antibody per tube was 1.2 micrograms). Samples were incubated at 4 degrees for 30 minutes. After the addition of 4 ml staining buffer, samples were pelleted as described above.

After removal of the $2^{nd}$ wash supernatant, the samples were resuspended in 50 microliters of 5% normal goat serum in PBS containing 0.25 micrograms of the secondary antibody (Molecular Probes goat antimouse IgG1 labeled with alexa 647). Samples were incubated at 4 degrees for 30 minutes in the dark, and washed with the addition of 4 ml staining buffer and pelleting as described above. The supernatant was decanted and the samples were resuspended in 300 microliters of staining buffer plus 0.5% paraformaldehyde for flow acquisition on a FACScalibur machine. The results were analyzed using Flojo software. In this experiment, 69% of the total cells were viable after the trypsin dissociation. Of these viable cells, 8.9% were stained with an antibody against the cardiomyocyte specific protein cardiac troponin I (see FIG. 2).

Example 3

Example of a Four-Phase Centrifugation Separation Method Enrichment

Cardiomyocytes were generated from hES cells of the H7 line by forming embryoid bodies for 4 days, and then proliferating on gelatin-coated plates for 17 days (5-aza-deoxycytidine and growth factors were not used). The cells were then dissociated using collagenase B, resuspended in differentiation medium. The cell suspension was then layered onto a discontinuous gradient of Percoll, and centrifuged at 1500 g for 30 min. Four fractions were collected: I. The upper interface; II. The 40.5% layer; III. The lower interface; IV. The 58.5% layer. The cells were washed and resuspended in differentiation medium. Cells for immunostaining were seeded into chamber slides at $10^4$ cells per well, cultured for 2 or 7, and then fixed and stained.

Results are shown in Table 3. Percentage of MHC positive cells was determined by counting cells in 30 images from triplicate wells for each fraction and presented as mean±standard deviation of cells from 3 wells.

TABLE 3

Percoll Separation

| | | | % staining for MHC | |
|---|---|---|---|---|
| Fraction | Cell Count | Beating Cells | Day 2 | Day 7 |
| Before separation | | + | 17 ± 4.4% | 15 ± 4% |
| I | 9.0 × 10⁶ | ± | 2.6 ± 0.5% | 2.5 ± 3.0% |
| II | 1.6 × 10⁶ | + | 4.5 ± 1.5% | 2.4 ± 0.9% |
| III | 4.0 × 10⁶ | ++ | 35.7 ± 2.7% | 28.3 ± 9.4% |
| IV | 1.3 × 10⁶ | +++ | 69. ± 5.0% | 52.2 ± 14.5% |

Beating cells were observed in all fractions, but Fractions III and IV contained the highest percentage.

Phenotype of the cells as determined by indirect immunocytochemistry is shown in Table 4.

TABLE 4

Characteristics of Separated Cell Populations

| Epitope | Cardiomyocyte-lineage | Non-cardiac cells |
|---|---|---|
| cTnI | ++ | − |
| cardiac-specific α/β MHC | ++ | − |
| cardiac β MHC | ++ | − |
| sarcomeric MHC | ++ | − |
| N-cadherin | ++ | ± |
| smooth muscle actin | ++ | subset |
| myogenin | − | − |
| α-fetoprotein | − | − |
| β-tubulin III | − | − |
| Ki67 | subset | subset |
| BrdU | subset | subset |
| SSEA-4 | − | − |
| Tra-1-81 | − | − |

Cardiomyocyte populations separated by density gradient centrifugation could be distinguished by staining for cTnI and MHC. Absence of staining for myogenin, α-fetoprotein, or β-tubulin III showed the absence of skeletal muscle, endoderm cell types, and neurons. Lack of staining for SSEA-4 and Tra-1-81 confirms the absence of undifferentiated hES cells.

α-Smooth muscle actin (SMA) is reportedly present in embryonic and fetal cardiomyocytes, but not adult cardiomyocytes (Leor et al., Circulation 97:I1332, 1996; Etzion et al., Mol. Cell Cardiol. 33:I321, 2001). Virtually all cTnI-positive cells and a subset of cTnI negative cells obtained in the cardiomyocyte differentiation protocol were positive for SMA, suggesting that they may be at an early stage and capable of proliferation.

Cells in fraction III and IV were replated, cultured for an additional 2 days. 43±4% of the MHC positive cells expressed BrdU, indicating that they were in the S phase of the cell cycle. In other experiments, a subset of cTnI-positive cells were found to express Ki-67. These results show that about 20% or 40% of the cardiomyocytes in the population were undergoing active proliferation.

Example 4

Example of Enrichment of Contracting Cells by Making Cardiac Bodies

This example illustrates the subsequent culturing of cardiomyocyte clusters as cardiac bodies to enrich for cells having characteristics desirable for therapeutic use and other purposes.

Three 225 cm² flasks of undifferentiated hES cells of the H7 line were used to generate embryoid bodies as already described. The EBs from each flask were resuspended in 75 mL of medium and transferred to three low adhesion six well plates (4 mL cell suspension per well), yielding nine plates of EBs in suspension in total. The EBs were re-fed after one day in suspension by transferring the newly formed EBs to 50 mL conical tubes (one plate per tube), letting the EBs settle at room temperature without agitation for 10 to 20 min, then removing the medium and replacing with fresh medium (25 mL per tube).

The EBs were returned to their original low attachment plates and maintained in suspension in 20% FBS containing medium for 3 additional days, then transferred to a total of three gelatin-coated 225 cm² tissue culture flasks. Two days after transfer to the gelatin coated flasks, the medium was removed and each flask was re-fed with 75 mL 20% FBS containing medium. Similar re-feedings occurred on day 8, 11, 13, 15, and 18. On day 20, the differentiated cultures were dissociated with Blendzyme (Roche Applied Sciences, Penzberg, Del.) and fractionated on discontinuous Percoll gradients as before. Fraction IV (the highest density fraction) was recovered and counted, yielding ~3.7×10⁶ single cells and small clusters.

The Fraction IV cells were resuspended in ~6.5 mL of 20% FBS containing medium, transferred to a 15 mL conical tube, and allowed to settle at room temperature without agitation for 10 min. The medium (containing 2.8×10⁶ cells, which is most of the single cells) was removed and replaced with fresh medium. The cell suspension was transferred to a single low attachment six well plate (~4 mL of cell suspension per well). The CBs were re-fed in a similar manner (transfer to 50 mL tube, settling for 10 min, medium removal and replacement) every 48 h.

Figure 3:
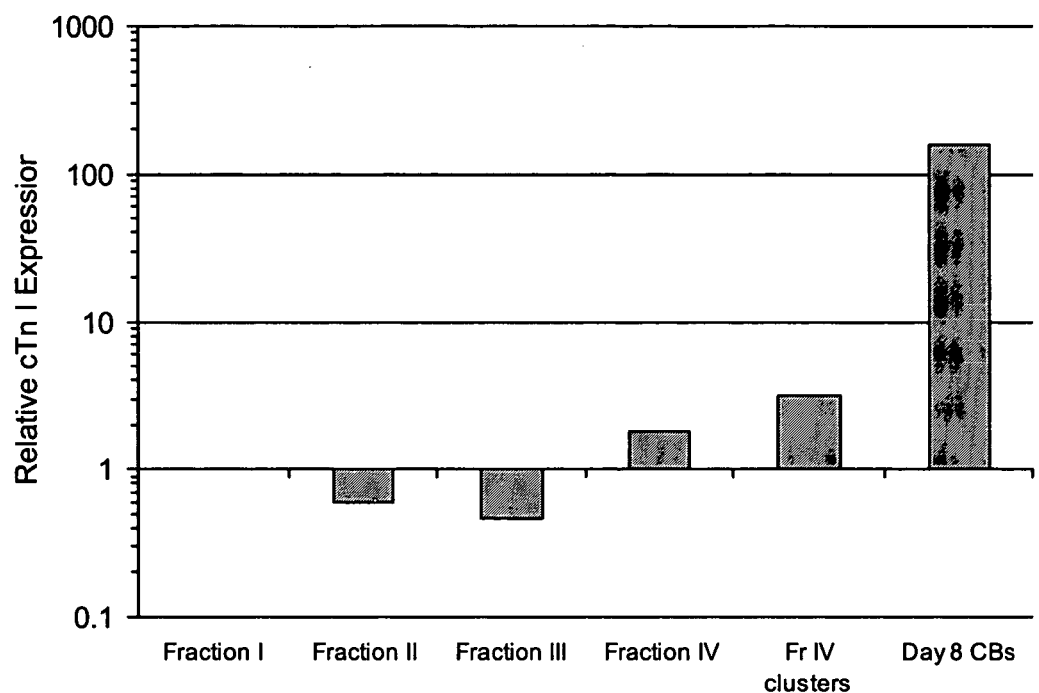
FIG. 3 shows the expression of cTnI measured in cardiac bodies formed from each of the four Percoll fractions. Undifferentiated hES cells are used as a negative control. Culturing the Fraction IV cells as cardiac bodies enriched for αMHC or cTnI expression by 100- to 500-fold.
Figure 3:
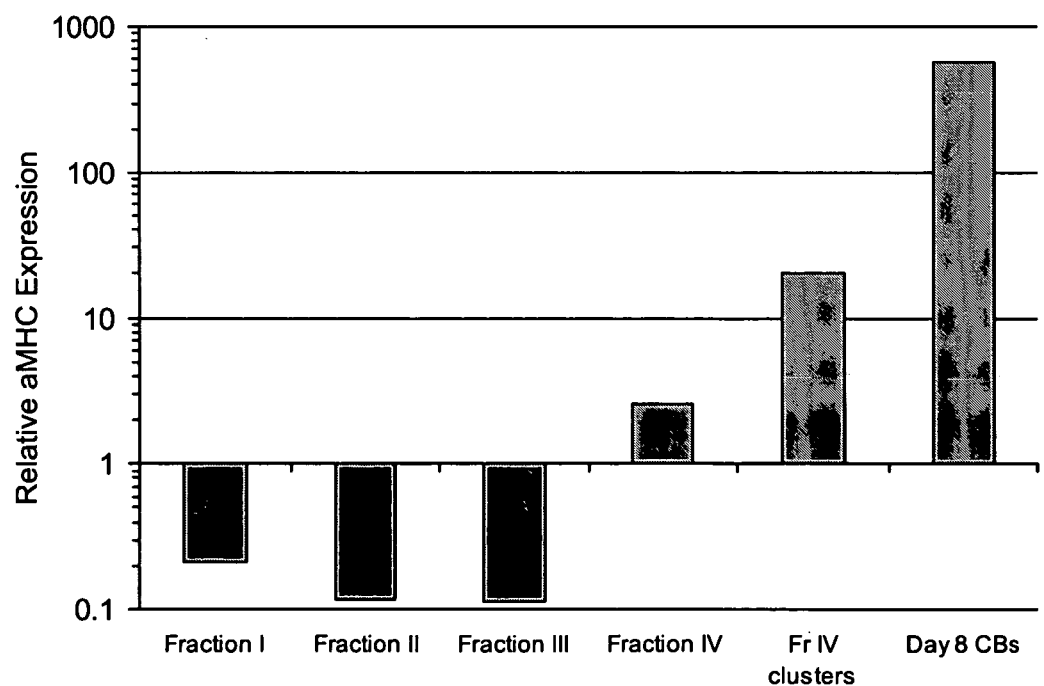

FIG. 3 shows the expression of the sarcomeric genes αMHC and cardiac troponin I as measured by real-time PCR. Relative to the expression after 20 days of culture on gelatin, separating the cells by Percoll increased expression by 2-5 fold in Fraction IV cells. Removing the single cells and collecting clusters increased expression to 5-20 fold. After 8 days of culturing the cells as cardiac bodies, the expression was 100- to 500-fold higher than the unseparated cells.

When CBs are replated onto gelatin or Matrigel, the clusters adhere, flatten, and produce large patches of spontaneously contracting cells. For use in animal testing, the cardiac bodies may be implanted directly, or dispersed into suspensions of single cells.

Example 5

Figure 4:
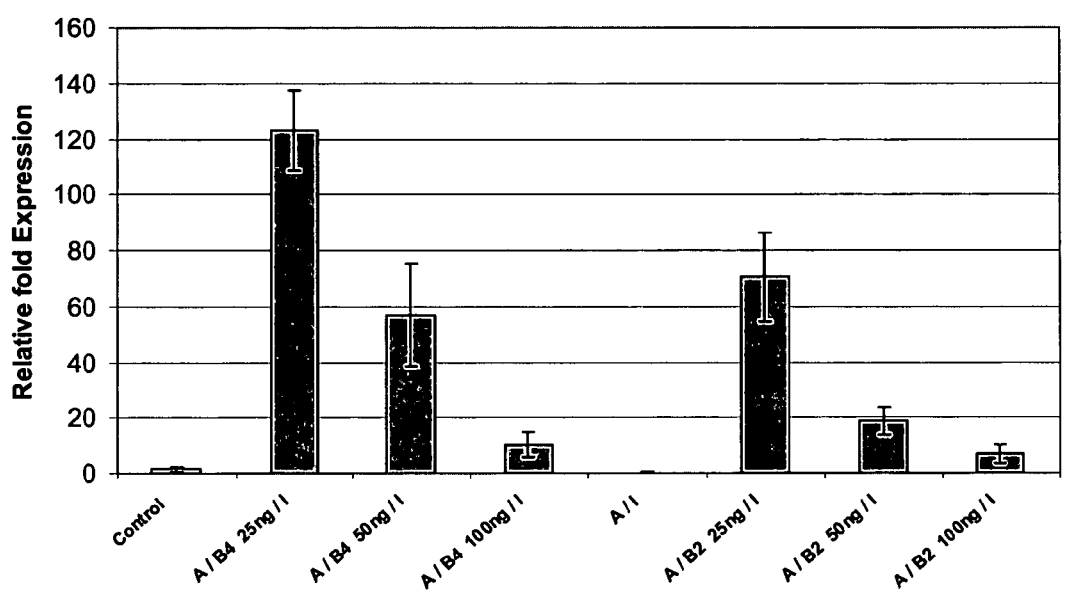
FIG. 4 shows the expression of αMHC in cell populations that result from the differentiation of hES cells using different concentrations of BMP-2 and BMP-4.

A differentiation of H7 hES cells was performed as in Example 1, except that the differentiation was performed in a 24-well plate instead of a 6-well plate and the volume for the factors was 1 ml per well. In addition, BMP-2 and BMP-4 were used at concentrations of 25 ng/ml, 50 ng/ml, and 100 ng/ml. Each concentration was done in triplicate. FIG. 4 shows the results expressed as a relative fold of the control, which involved performing the protocol but without the addition of an Activin, a BMP, or IGF-I. It can be seen that BMP-2 is also effective in the differentiation protocol.

Example 6

A 6-well plate of confluent H7 hES cells were washed with 2 ml PBS. Then, 2 ml of 0.5 mM EDTA in PBS was added to each well, and the plate was incubated for 10 minutes in 37° C. The EDTA solution was replaced with 1 ml mouse embryonic fibroblast-conditioned medium (MEF-CM) plus 8 ng/ml bFGF ("Medium A"). The undifferentiated ES cells were detached by pipetting 2-3 times and then seeded onto a 24-well plate at 400,000 cells/well in Medium A. The cells were incubated for two days at 37° C.

To induce the hES cells to differentiate, Medium A was replaced with 0.5 ml of B27:RPMI (1:50) (both reagents from Invitrogen) with 100 ng/ml Activin A (R&D Systems) ("Medium B") per well of 24-well plate. The cells were incubated for 24 hours. Medium B was then replaced with 10 ng/ml BMP-4 (R&D Systems) in 1:50 B27:RPMI ("Medium C") at 1 ml per well of a 24-well plate. The cells were incubated for 4 days.

Medium C was replaced with 1 ml of 1:50 B27:RPMI per well of the 24-well plate, and the plate was incubated for 15 days. The resulting cells were analyzed by FACS as in Example 2, except that the cells were incubated in the 0.25% trypsin/500 mM EDTA solution for 5 minutes instead of the 20 minutes used in Example 2. About 36% of the cells expressed cTnI.

The invention claimed is:

1. A method for obtaining a population of cells comprising α myosin heavy chain (αMHC) expressing cells from human embryonic stem (hES) cells by direct differentiation, comprising a) culturing the hES cells in the presence of Activin A in the absence of a BMP; b) subsequently culturing the cells in the presence of a BMP and in the absence of Activin A for between three and five days, wherein the BMP is selected from the group consisting of BMP-2 and BMP-4 and c) subsequently culturing the cells in the presence of an insulin like growth factor (IGF) in the absence of Activin A or a BMP, wherein the IGF is selected from the group consisting of IGF-I and IGF-II, thereby producing a cell population comprising α myosin heavy chain (αMHC) expressing cells.

2. The method of claim 1, wherein the BMP of step b) is BMP-4.

3. The method of claim 1, wherein the hES cells are cultured in the presence of Activin A for about one day and then subsequently cultured in the presence of the BMP for about four days.

4. The method of claim 1, wherein the culturing of step c) is performed for at least one week.

5. The method of claim 1, wherein the culturing of step c) is performed for at least two weeks.

6. The method of claim 1, wherein the IGF of step c) is IGF-I.

7. The method of claim 1, wherein the method does not comprise a step in which embryoid bodies are formed.

8. The method of claim 1, wherein the method further comprises harvesting cells from the culture subsequent to the IGF culturing step and enriching the harvested cell population for α myosin heavy chain (αMHC) expressing cells.

9. The method of claim 8, wherein the harvested cell population is enriched by a density gradient.

10. The method of claim 8, wherein the enriching the harvested cell population of α myosin heavy chain (αMHC) expressing cells comprises the formation of clusters of cells.

11. A method for obtaining an enriched population of α myosin heavy chain (αMHC) expressing cells from hES cells by direct differentiation, comprising a) culturing the hES cells in a serum-free medium in the presence of Activin A in the absence of a BMP for about one day; b) subsequently culturing in a serum-free medium in the presence of BMP-4 in the absence of Activin A for about four days; c) subsequently culturing in a serum-free medium in the presence of IGF-I for about five days or more; d) harvesting cells from the culture and e) enriching the harvested cell population for α myosin heavy chain (αMHC) expressing cells, thereby producing an enriched population of α myosin heavy chain (αMHC) expressing cells.

12. A method for obtaining a population of cells comprising α myosin heavy chain (αMHC) expressing cells from cells expressing stage specific embryonic antigen 3 (SSEA3), stage specific embryonic antigen 4 (SSEA4) and markers Tra-1-60 and Tra-1-81 by direct differentiation, comprising a) culturing the cells expressing stage specific embryonic antigen 3 (SSEA3), state stage specific embryonic antigen 4 (SSEA4) and markers Tra-1-60 and Tra-1-81 in the presence of Activin A in the absence of a BMP; b) subsequently culturing the cells in the presence of BMP-2 or BMP-4 and the absence of Activin A for between three and five days; and c) subsequently culturing the cells in the presence of an IGF in the absence of Activin A or a BMP wherein the IGF is selected from the group consisting of IGF-I and IGF-II, thereby producing a cell population comprising α myosin heavy chain (αMHC) expressing cells.

13. The method of claim 12, wherein the BMP of step b) is BMP-4.

14. The method of claim 12, wherein the cells expressing stage specific antigen embryonic antigen 3 (SSEA3), stage specific antigen embryonic antigen 4 (SSEA4) and markers Tra-1-60 and Tra-1-81 are cultured in the presence of Activin A for about one day and then subsequently cultured in the presence of the BMP for about four days.

15. The method of claim 12, wherein the culturing in the presence of an IGF is performed for at least one week.

16. The method of claim 12, wherein the culturing in the presence of an IGF is performed for at least two weeks.

17. The method of claim 12, wherein the IGF is IGF-I.

18. The method of claim 1, wherein the α myosin heavy chain (αMHC) expressing cells express cardiac troponin I.

19. The method of claim 11, wherein the α myosin heavy chain (αMHC) expressing cells express cardiac troponin I.

20. The method of claim 12, wherein the α myosin heavy chain (αMHC) expressing cells express cardiac troponin I.

21. The method of claim 1, wherein the α myosin heavy chain (αMHC) expressing cells beat in culture.

22. The method of claim 11, wherein the α myosin heavy chain (αMHC) expressing cells beat in culture.

23. The method of claim 12, wherein the α myosin heavy chain (αMHC) expressing cells beat in culture.

* * * * *